US012644872B2

(12) United States Patent
Lee et al.

(10) Patent No.: US 12,644,872 B2
(45) Date of Patent: Jun. 2, 2026

(54) APPARATUS FOR MEASURING ODOR

(71) Applicants:HYUNDAI MOTOR COMPANY,
Seoul (KR); KIA CORPORATION,
Seoul (KR)

(72) Inventors: Tae Hee Lee, Yongin-si (KR); **Dae Un
Sung**, Incheon (KR)

(73) Assignees: HYUNDAI MOTOR COMPANY,
Seoul (KR); KIA CORPORATION,
Seoul (KR)

( * ) Notice: Subject to any disclaimer, the term of this
patent is extended or adjusted under 35
U.S.C. 154(b) by 285 days.

(21) Appl. No.: 18/529,769

(22) Filed: Dec. 5, 2023

(65) Prior Publication Data

US 2025/0027924 A1      Jan. 23, 2025

(30) Foreign Application Priority Data

Jul. 19, 2023     (KR) ........................ 10-2023-0093468

(51) Int. Cl.
G01N 33/00          (2006.01)
G01N 1/42           (2006.01)
G01N 1/44           (2006.01)
(52) U.S. Cl.
CPC ........... G01N 33/0027 (2013.01); G01N 1/42
(2013.01); G01N 1/44 (2013.01)
(58) Field of Classification Search
CPC ........ G01N 33/0027; G01N 1/42; G01N 1/44;

G01N 1/2226; G01N 33/0006; G01N
33/0031; G01N 27/26; G01N 33/0016;
G01N 33/0063; G01N 33/0067; G01N
33/0044; G01N 33/0042; G01N 33/007;
G01N 33/0072; G01N 33/0073
USPC ......... 73/1.02, 1.03, 10.6, 1.07, 23.3, 23.31,
73/23.34, 24.1, 24, 6, 31.02, 31.5, 865.7
See application file for complete search history.

(56) References Cited

U.S. PATENT DOCUMENTS

2019/0227042 A1*   7/2019  Hashizume .......... G01N 27/407
2020/0400631 A1*  12/2020  Gao ....................... G01N 33/00
2022/0324721 A1*  10/2022  Ishikura ............. C01G 49/0018

FOREIGN PATENT DOCUMENTS

CN          113495123 A   * 10/2021   ......... G01N 33/0006
CN          115236135 A   * 10/2022   ............. G01N 27/04
WO    WO-2018206385 A1   * 11/2018   ......... G01N 33/0006

* cited by examiner

*Primary Examiner* — Robert R Raevis
(74) *Attorney, Agent, or Firm* — MCDONNELL
BOEHNEN HULBERT & BERGHOFF LLP

(57)          ABSTRACT
An apparatus for measuring an odor is capable of accurately
presetting a baseline that is utilized as a reference value for
an output value of an odor sensor, of computing a delta value
that represents a difference between the preset baseline and
an output value of the odor sensor that senses odor-mea-
surement-subject gas, and of determining the computed
delta value as a changed amount of the odor-measurement-
subject gas. With the apparatus, the accuracy of odor mea-
surement can be improved.

20 Claims, 13 Drawing Sheets

– OPERATION OF STORING INITIAL VALUE –

– OPERATION OF SETTING BASELINE USING PURE AIR –

– OPERATION OF STORING INITIAL VALUE –

– OPERATION OF SETTING BASELINE USING PURE AIR –

APPARATUS FOR MEASURING ODOR

CROSS REFERENCE TO RELATED APPLICATIONS

This application claims under 35 U.S.C. § 119 (a) the benefit of priority to Korean Patent Application No. 10-2023-0093468 filed on Jul. 19, 2023, the entire contents of which are incorporated herein by reference.

BACKGROUND

(a) Technical Field

The present disclosure relates to an apparatus for measuring an odor and, more particularly, to an apparatus for measuring an odor that is capable of accurately setting a baseline that is utilized as a reference value for an output value of an odor sensor, thereby improving the accuracy of odor measurement.

(b) Background Art

As well known, unique odors and volatile organic compounds (VOC) odors that are generated from various interiors of vehicles, such as seat covers, headliners, door trims, and mats, are the main causes of complaints about new cars.

Furthermore, grown mildews and nasty odors that are caused by condensed moisture in an evaporator core when a vehicular air conditioner operates are also the causes of discomfort to vehicle users.

In addition, depending on a surrounding environment during vehicle traveling, various nasty odors may be contained in outside air flowing into a vehicle, and these nasty odors from the outside can also cause discomfort to the vehicle users.

As such, the vehicular quality can be reduced due to various odors that occur both inside and outside the vehicle.

Therefore, in order to analyze and remove the causes of these odors occurring inside and outside the vehicle, first of all, there is a need for an odor sensor to accurately measure the odors and there is a need to collect the resulting odor data. Furthermore, there is also a need for a process or the like of accurately determining the actual causes of the occurrence of the odors by analyzing components and concentrations of the odors occurring both inside and outside the vehicle.

In order to address complaints about odors that occur not only in vehicles but also various industrial sites, first of all, it is necessary to perform a process of installing odor sensors at these industrial sites and accurately measuring the components and concentrations of the odors.

To this end, in the related art, as odor sensors for measuring the odors that occur not only from the vehicle but also from the industrial sites, electric-chemical odor sensors and electric-chemical odor sensor arrays can be used. Alternatively, bio odor sensors, such as a bio peptide type sensor and a sensor that uses amino acids, can also be used.

For example, when odor-measurement-subject gas particles are adsorbed on a surface of an electric-chemical odor sensor, odor measurement can be performed in a manner that outputs an electrical signal. Similarly, when the odor-measurement-subject gas particles are adsorbed on a surface of the bio odor sensor, the odor measurement can be performed in a manner that varies in a color signal, a RGB signal, and a brightness signal according to the number of absorbed gas particles.

An apparatus for measuring an odor that includes this odor sensor is configured to fundamentally measure a changed amount of odor-measurement-subject gas.

For example, as illustrated in FIG. 1, when the odor sensor outputs to a controller an output value that results from sensing the concentration of the odor-measurement-subject gas, the controller computes a delta value that represents a difference between a baseline that is utilized as a reference value and the output value of the odor sensor and determines the computed delta value as the changed amount of the odor-measurement-subject gas.

When the baseline utilized as the reference value is not accurate, the delta value, which represents the difference between the baseline and the output value of the odor sensor, becomes inaccurate. As a result, there is a problem in that an error may occur in measurement accuracy of the changed amount of the odor-measurement-subject gas.

Therefore, among factors that ensure the measurement accuracy of the apparatus for measuring an odor, the most critical factor is to accurately set the baseline. Accordingly, there is a demand for a new technique for accurately setting the base line.

SUMMARY

An object of the present disclosure, which is conceived to solve the above-mentioned problem in the related art, is to provide an apparatus for measuring an odor, the apparatus being capable of accurately presetting a baseline that is utilized as a reference value for an output value of an odor sensor, of computing a delta value that represents a difference between the preset baseline and an output value of the odor sensor that senses odor-measurement-subject gas, and of determining the computed delta value as a changed amount of the odor-measurement-subject gas. With the apparatus, the accuracy of odor measurement can be improved.

In order to accomplish the above-mentioned object, according to an aspect of the present disclosure, there is provided an apparatus for measuring an odor, the apparatus including a pre-chamber, a pure air supply line coupled to one side of the pre-chamber, a gas inflow line for introducing odor-measurement-subject gas, the gas inflow line being coupled to the one side of the pre-chamber, a fresh air supply line coupled to the one side of the pre-chamber, a first valve mounted on an inlet port in the pure air supply line, a second valve mounted on an inlet port in the gas inflow line, a third valve mounted on an inlet port in the fresh air supply line, an odor sensor chamber, the pure air supply line, the gas inflow line, and the fresh air supply line being coupled to the odor sensor chamber in such a manner as to be enabled to be open into the odor sensor chamber; an odor sensor mounted inside the odor sensor chamber; and a controller configured to set a baseline that represents a reference value for an output value of the odor sensor that senses the odor-measurement-subject gas, based on a signal that results from the odor sensor sensing pure air or fresh air that is supplied to the odor sensor chamber.

The apparatus may further include a gas flow line, one end being coupled to the pure air supply line, the gas inflow line, and the fresh air supply line in such a manner as to be enabled to be open into the pure air supply line, the gas inflow line, and the fresh air supply line, and the other end being coupled to the other side of the pre-chamber; a coupling pipe coupled between the gas flow line and the odor sensor chamber in such a manner as to be enabled to be open into each other; and a pure air supply tank coupled to the pure air supply line.

In the apparatus, the controller may be configured to open the first valve while closing the second valve and the third valve, so that the pure air is supplied from the pure air supply line to the odor sensor chamber and to store as an initial value an output value of the odor sensor that senses the pure air supplied to the odor sensor chamber.

In the apparatus, the controller may be configured to store as the initial value the output value of the odor sensor that senses the pure air, then to compare with the initial value subsequent output values of the odor sensor that senses the pure air at predetermined time intervals and to perform alarming control for replacement of the odor sensor when a difference between the subsequent output value of the odor sensor and the initial value is at a predetermined level or higher.

In the apparatus, the controller may be configured to open the third valve while closing the first valve and the second valve, so that the fresh air that is outside air is supplied from the fresh air supply line to the odor sensor chamber and to set a baseline that is utilized as the reference value, as an output value of the odor sensor that senses the fresh air supplied to the odor sensor chamber.

In the apparatus, the controller may be configured to open the second valve while closing the first valve and the third valve, so that the odor-measurement-subject gas is supplied from the gas supply line to the odor sensor chamber, to compute a delta value that represents a difference between an output value of the odor sensor that senses the odor-measurement-subject gas supplied to the odor sensor chamber and a baseline that represents the reference value, and to determine the computed delta value as a changed amount of the odor-measurement-subject gas.

In the apparatus, the controller may be configured to open the first valve while closing the second valve and the third valve in a case where odor measurement is necessary at a location where the fresh air that is outside air is contaminated, so that the pure air is supplied from the pure air supply line to the odor sensor chamber and to set a baseline that is utilized as the reference value, as an output value of the odor sensor that senses the pure air supplied to the odor sensor chamber.

In the apparatus, an intake pump for introducing the pure air, the odor-measurement-subject gas, and the fresh air into the odor sensor chamber may be coupled to an outlet port formed in the other side of the odor sensor chamber.

In the apparatus, a first heater that is turned on and off by the controller in order to heat gas or air that flows through the gas flow line, and a first cooler that is turned on and off by the controller in order to cool the gas or the air that flows through the gas flow line, may be mounted on the pre-chamber.

In the apparatus, a second heater that is turned on and off by the controller in order to heat the inside of the odor sensor chamber, and a second cooler that is turned on and off by the controller in order to cool the inside of the odor sensor chamber, may be mounted on the odor sensor chamber.

In order to accomplish the above-mentioned object, according to another aspect of the present disclosure, there is provided an apparatus for measuring an odor, the apparatus including a pre-chamber, a pure air supply line coupled to one side of the pre-chamber, a gas inflow line for introducing odor-measurement-subject gas, the gas inflow line being coupled to the one side of the pre-chamber, a first valve mounted on an inlet port in the pure air supply line, a second valve mounted on an inlet port in the gas inflow line, a first odor sensor chamber, the pure air supply line and the gas inflow line being coupled to the first odor sensor chamber in such a manner as to be enabled to be open into the first odor sensor chamber, a first odor sensor mounted inside the first odor sensor chamber, a second odor sensor chamber employing a structure in which a fresh-air inlet port and a fresh-air outlet port are formed in one side and the other side, respectively, of the second odor sensor chamber, the second odor sensor chamber being separately mounted at an outside position where fresh air is seamlessly introduced; a second odor sensor mounted inside the second odor sensor chamber, and a controller configured to set a baseline that represents a reference value for an output value of the first odor sensor that senses the odor-measurement-subject gas, based on a signal that results from the first odor sensor sensing pure air that is supplied to the first odor sensor chamber or a signal that results from the second odor sensor sensing the fresh air that is supplied to the second odor sensor chamber.

The apparatus may further include a gas flow line, one end being coupled to the pure air supply line and the gas inflow line in such a manner as to be enabled to be open into the pure air supply line and the gas inflow line and the other end being coupled to the other side of the pre-chamber, a coupling pipe coupled between the gas flow line and the first odor sensor chamber in such a manner as to be enabled to be open into each other, and a pure air supply tank coupled to the pure air supply line.

In the apparatus, the controller may be configured to open the first valve while closing the second valve, so that the pure air is supplied from the pure air supply line to the first odor sensor chamber and to store as an initial value an output value of the first odor sensor that senses the pure air supplied to the first odor sensor chamber.

In the apparatus, the controller may be configured to store as the initial value the output value of the first odor sensor that senses the pure air, then to compare with the initial value subsequent output values of the first odor sensor that sense the pure air at predetermined time intervals and to perform alarming control for replacement of the first odor sensor when a difference between the subsequent output value of the first odor sensor and the initial value is at a predetermined level or higher.

In the apparatus, the controller may be configured to set a baseline that is utilized as the reference value, as an output value of the second odor sensor that senses the fresh air supplied to the second odor sensor chamber.

In the apparatus, the controller may be configured to open the second valve while closing the first valve, so that the odor-measurement-subject gas is supplied from the gas supply line to the first odor sensor chamber, to compute a delta value that represents a difference between an output value of the first odor sensor that senses the odor-measurement-subject gas supplied to the first odor sensor chamber and a baseline that represents the reference value, and to determine the computed delta value as a changed amount of the odor-measurement-subject gas.

In the apparatus, the controller may be configured to open the first valve while closing the second valve in a case where odor measurement is necessary at a location where the fresh air that is outside air is contaminated, so that the pure air is supplied from the pure air supply line to the first odor sensor chamber and to set a baseline that is utilized as the reference value, as an output value of the first odor sensor that senses the pure air supplied to the first odor sensor chamber.

In the apparatus, an intake pump for introducing the pure air and the odor-measurement-subject gas into the first odor sensor chamber may be coupled to an outlet port formed in the other side of the first odor sensor chamber.

In the apparatus, a first heater that is turned on and off by the controller in order to heat gas or air that flows through the gas flow line, and a first cooler that is turned on and off by the controller in order to cool the gas or the air that flows through the gas flow line, may be mounted on the pre-chamber.

In the apparatus, a second heater that is turned on and off by the controller in order to heat the inside of the first odor sensor chamber, and a second cooler that is turned on and off by the controller in order to cool the inside of the first odor sensor chamber may be mounted on the first odor sensor chamber.

The apparatus for measuring an odor according to the present disclosure provides the following advantageous effects.

Firstly, the baseline that is utilized as the reference value for the output value of the odor sensor can be accurately preset, and the delta value that represents the difference between the preset baseline and the output value of the odor sensor that senses the odor-measurement-subject gas can be determined as the changed amount of the odor-measurement-subject gas, thereby improving the accuracy of the odor measurement.

Secondly, the first heater or the first cooler that is mounted on the pre-chamber is enabled to additionally operate, or the second heater or the second cooler that is mounted on the odor sensor chamber is enabled to additionally operate. Thus, the temperature and the humidity of the air or the gas that is supplied to the odor sensor chamber are adjusted to a level at which the odor sensor accurately performs the sensing, thereby improving the measurement accuracy of the odor sensor.

BRIEF DESCRIPTION OF THE FIGURES

The above and other features of the present disclosure will now be described in detail with reference to certain exemplary examples thereof illustrated in the accompanying drawings which are given herein below by way of illustration only, and thus are not limitative of the present disclosure, and wherein.

DETAILED DESCRIPTION

Figure 1:
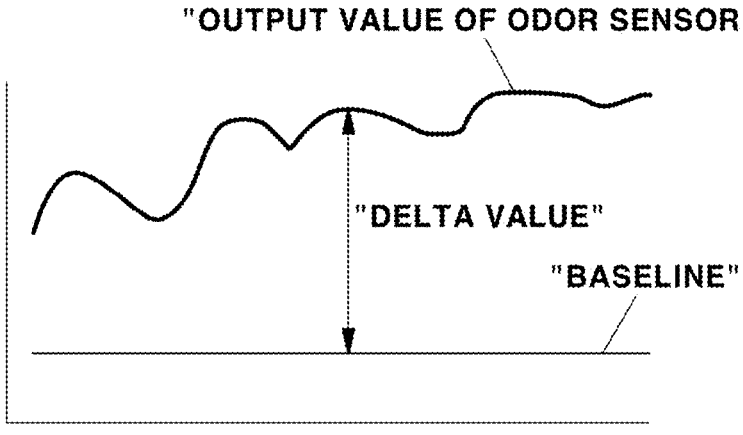
FIG. 1 is a graph that is referred to for description of a method in which an apparatus for measuring an odor measures a changed amount of odor-measurement-subject gas.
Figure 2:
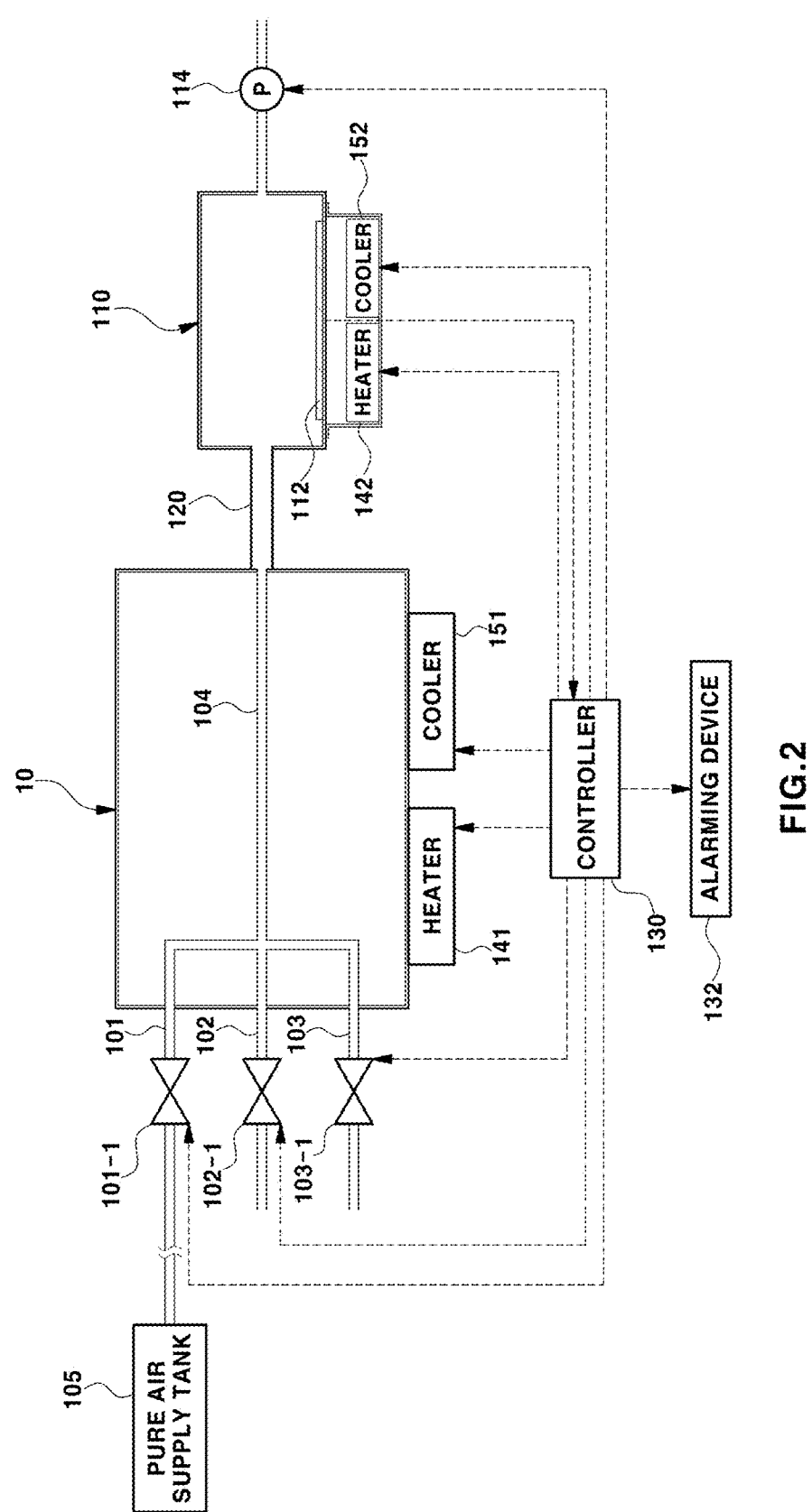
FIG. 2 is a schematic view illustrating an apparatus for measuring an odor according to a first embodiment of the present disclosure.

Embodiments of the present disclosure are described in an exemplary manner in terms of specific structures and functions for the purpose of supporting both written description and enablement requirements. The embodiments of the present disclosure may be implemented in various forms. However, the present disclosure should not be construed as being limited thereto. Furthermore, the present disclosure should be construed as including all modifications, equivalents, and substitutions that fall within the nature and gist of the present disclosure and the technical scope thereof.

Throughout the present specification, the terms first, second, and so forth may be used to describe various constituent elements, but do not impose any limitation thereon. These terms are used only to distinguish one constituent element from another. For example, a first constituent element may be named a second constituent element without departing from the scope of the claims that define the present disclosure. Likewise, the second constituent element may also be named the first constituent element.

It should be understood that, throughout the present specification, a constituent element, when referred to as being "coupled to" or "connected to" a different constituent element, may be directly coupled to or directly connected to the different constituent element or may be coupled to or connected to the different constituent element with an intervening constituent element in between. In contrast, it should be understood that a constituent element, when referred to as being "directly coupled to" or "directly connected to" a different constituent element, is coupled to or connected to the different constituent element without any intervening constituent element in between. Expressions such as "between" and "directly between," and "adjacent to" and "directly adjacent to" for describing a relationship between constituent elements should be construed in the same manner.

Like reference numerals depict like constituent elements throughout the present specification. The terms used throughout the present specification serve the purpose of describing the embodiments, but are not intended to impose any limitation on the present disclosure. Unless specially stated otherwise throughout the present specification, a singular noun or a singular noun phrase may have a plural meaning. The terms "comprise" and/or "comprising" used in the present specification should be construed to mean "including the following constituent element, step, operation, or element, but not excluding one or more other constituent elements, steps, operations, or elements."

Embodiments of the present description will be described in detail below with reference to the accompanying drawings.

First Embodiment

FIGS. 2 to 6 are views each illustrating an apparatus for measuring an odor according to the first embodiment of the present disclosure. Reference numerals 100 and 110 in the drawings depict a pre-chamber and an odor sensor chamber, respectively.

As illustrated in FIGS. 2 to 6, the pre-chamber 100 and the odor sensor chamber 110 are coupled to each other through a coupling pipe 120 in such a manner to be enabled to be open into each other.

A pure air supply line 101, a gas inflow line 102 for inflow of odor-measurement-subject gas, and a fresh air supply line 103 are in parallel coupled to one side of the pre-chamber 100.

At this point, a pure air supply tank 105 for supplying pure air (for example, pure carbon dioxide or pure nitrogen) is coupled to the pure air supply line 101. The gas inflow line 102 is arranged in an open state inside a space (for example, an in-vehicle space) where the odor-measurement-subject gas is present. The fresh air supply line 103 may be arranged in an open state in a manner that extends up to a location (for example, an air intake part through which outside air flows into a vehicle, a cowl panel communicating with the outside air, a sunroof or the like) into which outside air in a clear state can flow.

In addition, a first valve 101-1 for supplying or blocking the flow of the pure air is mounted in an opening- and closing-enabled manner on an inlet port in the pure air supply line 101. Likewise, a second valve 102-1 for supplying or blocking the flow of the odor-measurement-subject gas is mounted in an opening- and closing-enabled manner on an inlet port in the gas inflow line 102. Furthermore, a third valve 103-1 for supplying and blocking the flow of fresh air is mounted in an opening- and closing-enabled manner on an inlet port in the fresh air supply line 103.

FIGS. 1 to 6 and other figures illustrate that the first valve 101-1, the second valve 102-1, and the third valve 103-1 are mounted in a preferred manner outside the pre-chamber 100. However, they may be arranged to be mounted inside the pre-chamber 100.

An outlet port in the pure air supply line 101, an outlet port in the gas inflow line 102, and an outlet port in the fresh air supply line 103 each are coupled to the odor sensor chamber 110 through one gas flow line 104 in such a manner as to be enabled to be open into the odor sensor chamber 110.

To this end, one gas flow line 104 is arranged along a lengthwise direction of the pre-chamber 100 inside the pre-chamber 100. The outlet port in the pure air supply line 101, the outlet port in the gas inflow line 102, and the outlet port in the fresh air supply line 103 are coupled to one end of the gas flow line 104 in such a manner as to be enabled to be open into the gas flow line 104. The other end of the gas flow line 104 is coupled to the other side of the pre-chamber 100.

In addition, the gas flow line 104 and the odor sensor chamber 110 are coupled to each other through the coupling pipe 120 in such a manner as to be enabled to be open into each other.

An odor sensor 112 for sensing the pure air, the odor-measurement-subject gas, the fresh air, and the like is attached on an inner bottom surface of the odor sensor chamber 110. The odor sensor 112 may be one of an electro-chemical odor sensor, an electro-chemical odor sensor array, a bio-peptide type sensor, a sensor using amino acids, and other types of odor sensors.

In this case, the odor sensor 112 is coupled to the controller 130 in a manner that can transmit a sensing signal. Thus, the odor sensor 112 may transmit signals, that is, output values of the odor sensor 112 that senses the pure air, the odor-measurement-subject gas, the fresh air, and the like, to the controller 130.

Particularly, the controller 130 is configured to preset a baseline that represents a reference value, based on a signal that results from the odor sensor 112 sensing the pure air or the fresh air that is supplied to the odor sensor chamber 110. Furthermore, the controller 130 is configured to utilize the preset baseline as a reference value for the output value of the odor sensor 112 that senses the odor-measurement-subject gas.

Figure 4:
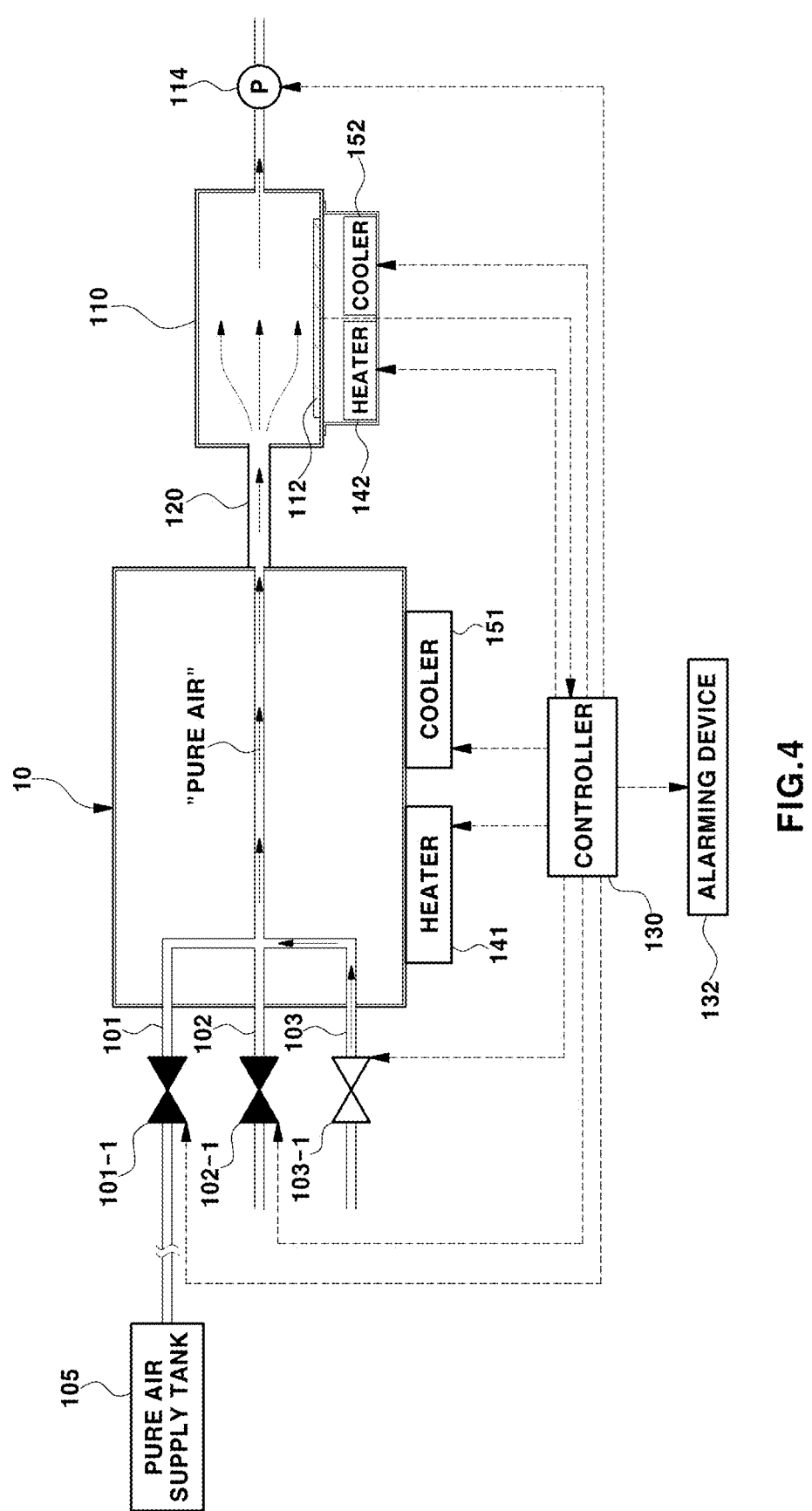

To this end, the controller 130, as illustrated in FIG. 4, is configured to open the third valve 103-1 while closing the first valve 101-1 and the second valve 102-1, so that the fresh air that is the outside air is supplied from the fresh air supply line 103 to the odor sensor chamber 110 through the gas flow line 104 and the coupling pipe 120. Furthermore, the controller 130 is configured to set the baseline that is utilized as the reference value, as an output value of the odor sensor 112 that senses the fresh air, which is supplied to the odor sensor chamber 110.

In contrast, odor measurement may be necessary at a location where the fresh air that is the outside air is contaminated. For example, the vehicle may pass by a livestock barn or passes through an industrial complex in which an odor occurs. In addition, the odor measurement may be necessary at a location where the fresh air that is the outside air is contaminated or absent, such as the inside of a manhole in which toxic gas is present, the inside of an airtight coal mine, the inside of an airtight submergence vehicle, the inside of an airtight submarine, the inside of an airtight spacecraft, the inside of an airtight space suit, or the like. In these cases, when the baseline that is utilized as the reference value is set as the output value of the odor sensor 112 that senses the fresh air, the baseline that is utilized as the reference value may not be accurate. Consequently, a delta value (a changed amount of the odor-measurement-subject gas) that represents a difference between the baseline and the output value of the odor sensor 112 may be inevitably inaccurate as before.

To solve this problem, in a case where the odor measurement is necessary at the location where the fresh air is contaminated or absent, a user can instruct the controller 130 to set the baseline based on the pure air, using an input means (for example, a switch or a menu button that is installed in the vehicle, or a corresponding application installed on a smart device).

Figure 6:
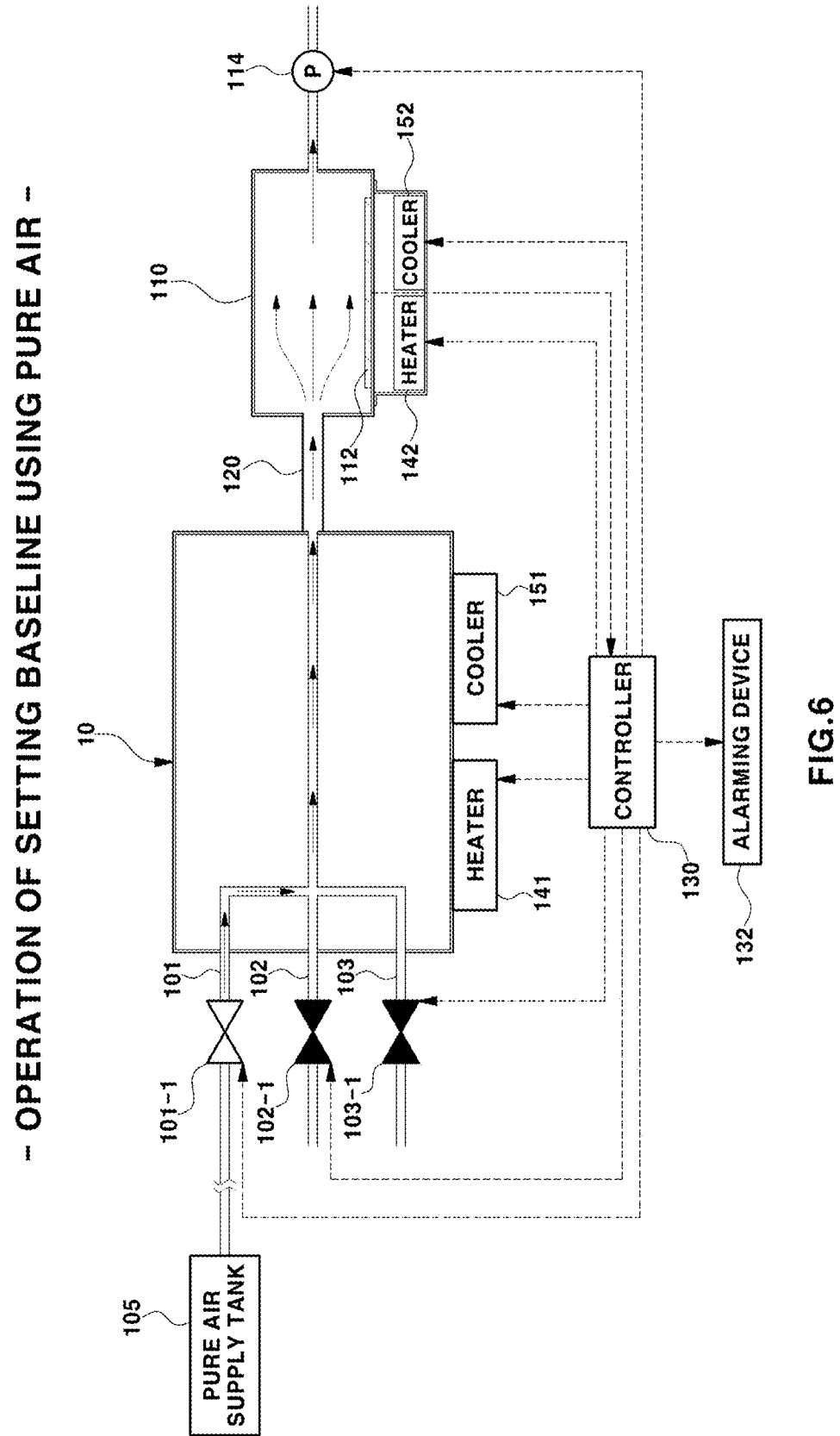

Accordingly, as illustrated in FIG. 6, the controller 130 is configured to open the first valve 101-1 while closing the second valve 102-1 and the third valve 103-1, in the case where the odor measurement is necessary at the location where the fresh air is contaminated or absent, so that the pure air is supplied from the pure air supply line 101 to the odor sensor chamber 110 through the gas flow line 104 and the coupling pipe 120. Furthermore, the controller 130 is configured to set the baseline that is utilized as the reference value, as an output value of the odor sensor 112 that senses the pure air supplied to the odor sensor chamber 110.

As described above, after the baseline is set, a process of measuring an odor that is present in a specific internal space (for example, a space inside the vehicle, or the like) may be performed.

Figure 5:
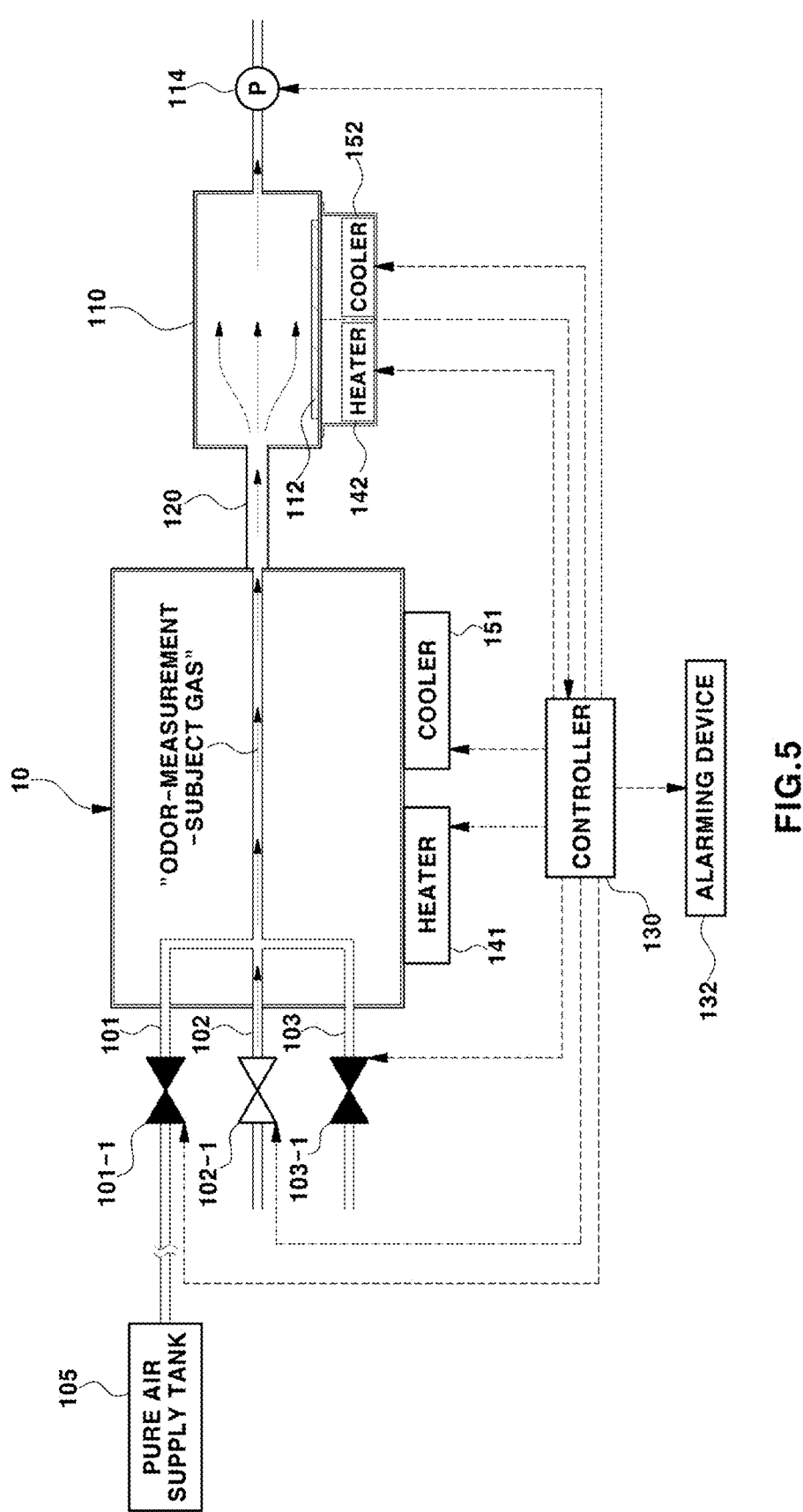

To this end, as illustrated in FIG. 5, the controller 130 is configured to open the second valve 102-1 while closing the first valve 101-1 and the third valve 103-1, so that the odor-measurement-subject gas is supplied from the gas inflow line 102 to the odor sensor chamber 110 through the gas flow line 104 and the coupling pipe 120. Furthermore, the controller 130 is configured to compute a delta value that represents a difference between an output value of the odor sensor 112 that senses the odor-measurement-subject gas supplied to the odor sensor chamber 110 and the baseline that represents the reference value and to determine the computed delta value as the changed amount of the odor-measurement-subject gas.

In a case where the odor sensor 112 is initially attached inside the odor sensor chamber 110, in order to manage the lifetime and durability of the odor sensor 112, it is preferred that an initial output value of the odor sensor 112 is stored in the controller 130.

Figure 3:
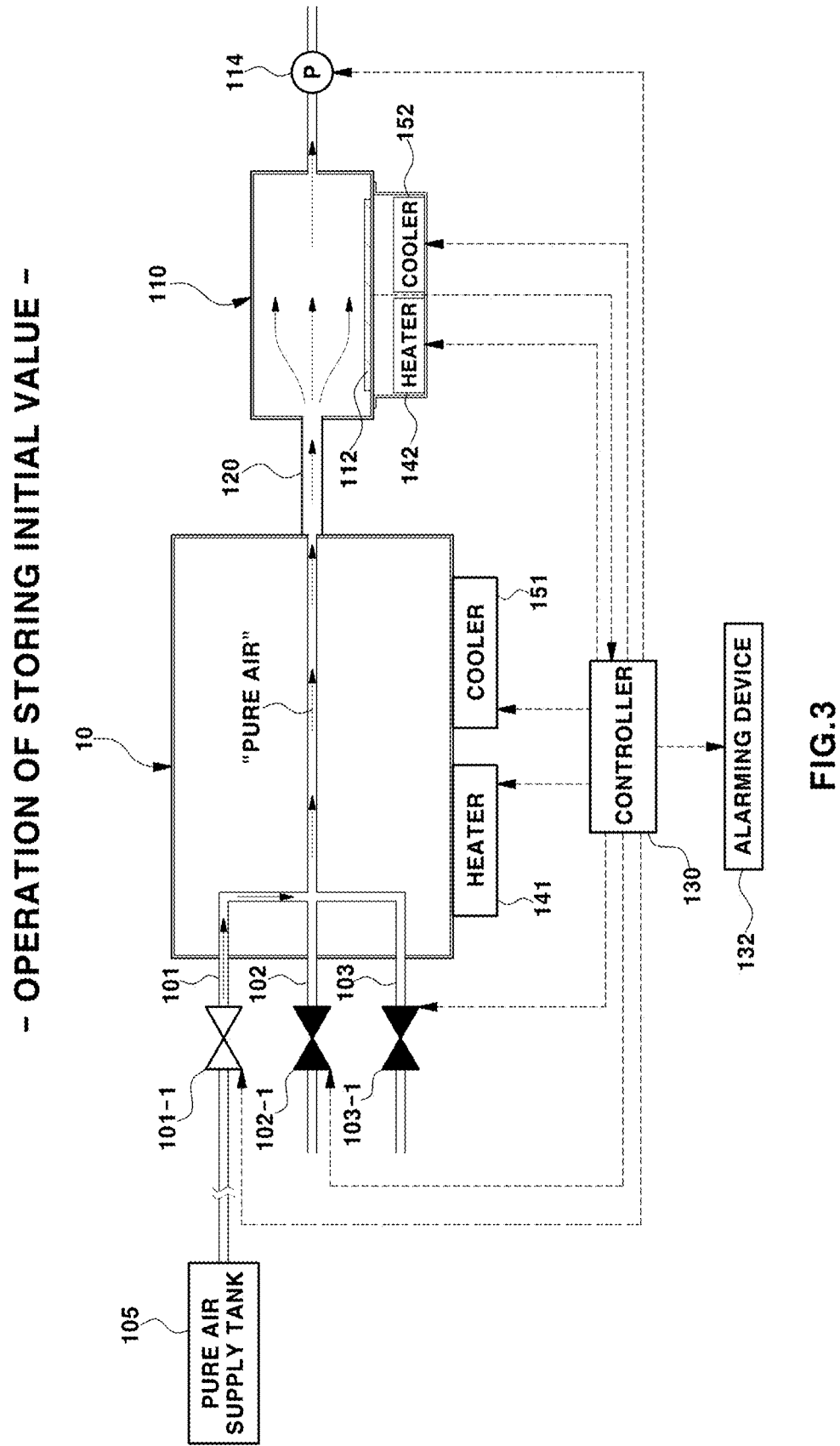
FIGS. 3, 4, 5, and 6 are schematic views each illustrating a state where the apparatus for measuring an odor according to the first embodiment of the present disclosure operates for odor measurement.

To this end, as illustrated in FIG. 3, the controller 130 is configured to open the first valve 101-1 while closing the second valve 102-1 and the third valve 103-1, in the case where the odor sensor 112 is initially attached inside the odor sensor chamber 110, so that the pure air is supplied from the pure air supply line 101 to the odor sensor chamber 110 through the gas flow line 104 and the coupling pipe 120. Furthermore, the controller 130 is configured to store the output value of the odor sensor 112 that senses the pure air supplied to the odor sensor chamber 110, as an initial value.

In this case, the more accumulated the usages of the odor sensor 112, the more cracks occur on a surface of the odor sensor 112, or the more foreign materials (dusts, gas particles, and the like) that cause a decrease in sensing performance build up on the surface of the odor sensor 112. For these reasons, the odor sensor 112 decreases in performance. Therefore, it is necessary to accurately determine a period with which the odor sensor 112 is replaced.

To this end, the controller 130 may store as the initial value the output value of the odor sensor 112 that senses the pure air and then controls the first valve 101-1 in an open manner while controlling the second valve 102-1 and the third valve 103-1 in a closed manner, so that the pure air is supplied at predetermined time intervals to the odor sensor chamber 110. Thus, the odor sensor 112 may sense the pure air at the predetermined time intervals.

Therefore, the controller 130 is configured to store as the initial value the output value of the odor sensor 112 that senses the pure air and then to compare with the initial value subsequent output values of the odor sensor 112 that senses the pure air at predetermined time intervals. Furthermore, the controller 130 is configured to determine replacement of the odor sensor 112 due to a decrease in performance of the odor sensor 2 and to perform alarming control for the replacement of the odor sensor 112 when a difference between the subsequent output value of the odor sensor 112 and the initial value is at a predetermined level or higher.

In this case, the controller 130 may instruct a visual or audio alarming device 132 to issue an alarming signal to perform the alarming control for the replacement of the odor sensor 112.

It is preferred that an intake pump 114 for introducing the pure air, the odor-measurement-subject gas and the fresh air into the odor sensor chamber 110 is coupled to an outlet port formed in the other side of the odor sensor chamber 110.

Accordingly, by driving the intake pump 114, the pure air, the odor-measurement-subject gas, and the fresh air can be easily introduced into the odor sensor chamber 110 and, after the odor sensor 112 performs sensing, can be discharged to the outside through the outlet port in the odor sensor chamber 110.

When the odor sensor 112 senses the pure air, the odor-measurement-subject gas, the fresh air, and the like, odor data that result from the measuring by the odor sensor 112 may vary with the temperature or humidity of air or gas. Consequently, the accuracy of the measurement by the odor sensor 112 may decrease. For this reason, it is preferred that the temperature or humidity of the air or gas (the pure air, the odor-measurement-subject gas, the fresh air, or the like) that is sensed by the odor sensor 112 is consistently adjusted.

To this end, in order to heat the gas or the air that flows through the gas flow line 104, a first heater 141 and a first cooler 151 are mounted on the pre-chamber 100. The first heater 141 is turned on and off by the controller 130. The first cooler 151 is turned on and off by the controller 130 in order to cool the gar or the air that flows through the gas flow line 104.

Accordingly, when the temperature of the air or gas (the pure air, the odor-measurement-subject gas, the fresh air, or the like) that flows through the gas flow line 104 is below a reference value, or when the humidity thereof is at or above the reference value, the controller 130 turns on and off the first heater 141 in order for the first heater 141 to perform a heating operation, based on a detection signal of a temperature and humidity sensor (not illustrated). In contrast, when the temperature of the air or gas (the pure air, the odor-measurement-subject gas, the fresh air, or the like) that flows through the gas flow line 104 is at or above the reference value, or when the humidity thereof is below the reference value, the controller 130 controls the first cooler 151 in a turn-on manner in order for the first cooler 151 to perform a cooling operation, based on the detection signal of the temperature and humidity sensor. Thus, the temperature and the humidity of the gas or the air that flows through the gas flow line 104 can be consistently adjusted.

It is preferred that the pre-chamber 100 is manufactured in such a manner to have a volume that facilitates transfer of warm air generated during heating or cold air generated during cooling to the gas or the air that flows through the gas flow line 104.

In this case, the temperature and the humidity of the air or gas (the pure air, the odor-measurement-subject gas, the fresh air, or the like) that flows through the gas flow line 104 are primarily adjusted by the first heater 141 or the first cooler 151, but may not be completely adjusted to a predetermined level.

Accordingly, a second heater 142 and a second cooler 152 may be further mounted at predetermined positions, respectively, on the odor sensor chamber 110. The second heater 142 is turned on and off by the controller 130 in order to heat the inside of the odor sensor chamber 110. The second cooler 152 is turned on and off by the controller 130 in order to cool the inside of the odor sensor chamber 110.

With this configuration, the temperature and the humidity of the air or gas (the pure air, the odor-measurement-subject gas, the fresh air, or the like) that flows through the gas flow line 104 are primarily adjusted by the first heater 141 or the first cooler 151 and then are supplied into the odor sensor chamber 110. Thereafter, the temperature and the humidity of the air or gas that is introduced into the odor sensor chamber 110 are secondarily adjusted by a heating operation of the second heater 142 and a cooling operation of the second cooler 152. Thus, the temperature and the humidity of the air or gas (the pure air, the odor-measurement-subject gas, the fresh air, or the like) that is sensed by the odor sensor 112 can be completely adjusted to a predetermined level. Accordingly, the accuracy of the odor data that result from the measuring by the odor sensor 112 can be ensured.

Sequential steps of the odor measurement by the apparatus for measuring an odor according to the first embodiment of the present disclosure are performed as follows.

Figure 7:
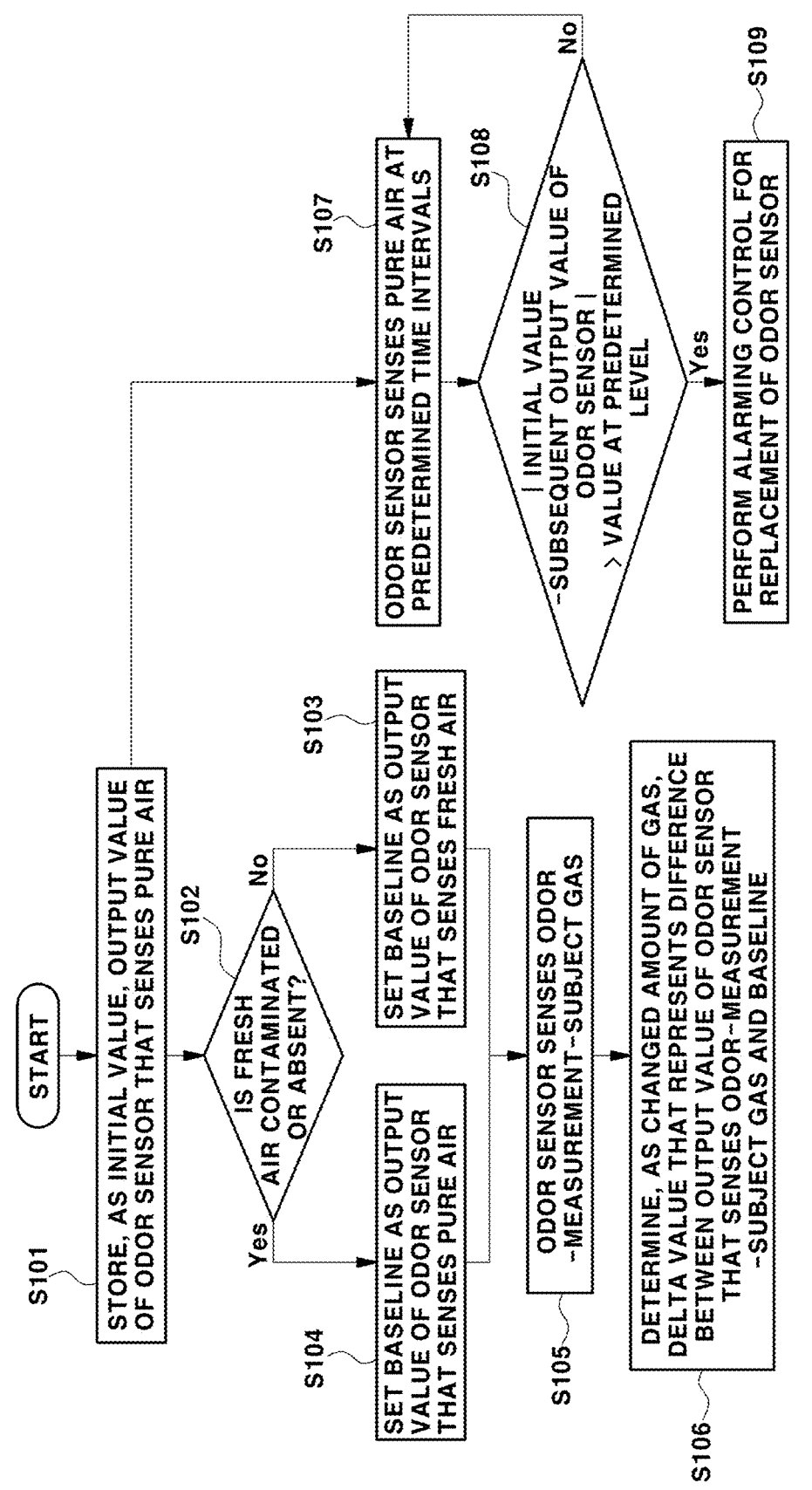
FIG. 7 is a flowchart illustrating a method of measuring an odor according to the first embodiment of the present disclosure.
Figure 8:
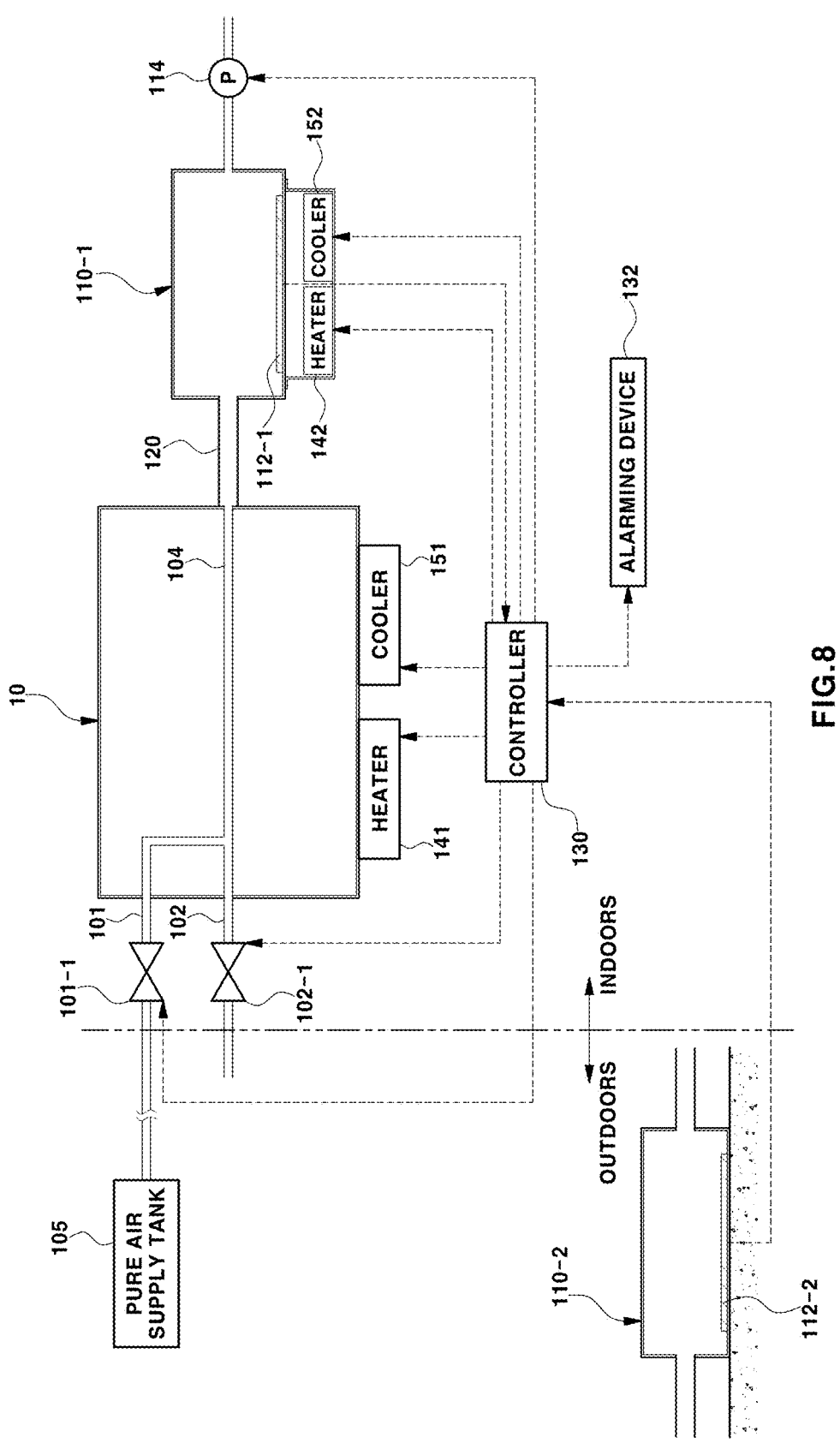
FIG. 8 is a schematic view illustrating an apparatus for measuring an odor according to a second embodiment of the present disclosure.

FIG. 7 is a flowchart illustrating a method of measuring an odor according to the first embodiment of the present disclosure.

First, in the case where the odor sensor 112 is initially attached inside the odor sensor chamber 110, the odor sensor 112 is set to sense the pure air, and the controller 130 stores as the initial value the output value of the odor sensor 112 that senses the pure air at S101.

To this end, as illustrated in FIG. 3, in the case where the odor sensor 112 is initially attached inside the odor sensor chamber 110, the controller 130 opens the first valve 101-1 while closing the second valve 102-1 and the third valve 103-1, so that the pure air is supplied from the pure air supply line 101 to the odor sensor chamber 110 through the gas flow line 104 and the coupling pipe 120. Furthermore, the controller 130 stores as the initial value the output value of the odor sensor 112 that senses the pure air supplied to the odor sensor chamber 110.

Subsequently, the user checks whether or not the fresh air that is the outside air is contaminated or whether or not the fresh air is absent at S102.

In a case where the result of the checking is that the fresh air that is the outside air is clean without being contaminated, the baseline is set as the output value of the odor sensor 112 that senses the fresh air at S103.

To this end, as illustrated in FIG. 4, the controller 130 may open the third valve 103-1 while closing the first valve 101-1 and the second valve 102-1, so that the fresh air that is the outside air is supplied from the fresh air supply line 103 to the odor sensor chamber 110 through the gas flow line 104 and the coupling pipe 120. Furthermore, the controller 130 may set the baseline that is utilized as the reference value, as the output value of the odor sensor 112 that senses the fresh air supplied to the odor sensor chamber 110 and may store the output value of the odor sensor 112.

In contrast, in a case where the fresh air that is the outside air is contaminated or absent, the baseline is set as the output value of the odor sensor 112 that senses the pure air at S104.

To this end, as illustrated in FIG. 6, the controller 130 may open the first valve 101-1 while closing the second valve 102-1 and the third valve 103-1, so that the pure air is supplied from the pure air supply line 101 to the odor sensor chamber 110 through the gas flow line 104 and the coupling pipe 120. Furthermore, the controller 130 may set the baseline that is utilized as the reference value, as the output value of the odor sensor 112 that senses the pure air supplied to the odor sensor chamber 110 and may store the output value of the odor sensor 112.

Next, odor-measurement-subject gases (for example, various nasty odors present inside the vehicle, nasty odors present in various industrial sites, and the like) are sensed at S105.

To this end, as illustrated in FIG. 5, the controller 130 opens the second valve 102-1 \while closing the first valve 101-1 and the third valve 103-1, so that the odor-measurement-subject gas is supplied from the gas inflow line 102 to the odor sensor chamber 110 through the gas flow line 104 and the coupling pipe 120. The odor sensor 112 senses the odor-measurement-subject gas that is supplied to the odor sensor chamber 110 and transmits the output value that results from the sensing, to the controller 130.

Subsequently, the controller 130 computes the delta value that represents the difference between the output value of the odor sensor 112 that senses the odor-measurement-subject gas and the baseline that represents the reference value, and determines the computed delta value as the changed amount of the odor-measurement-subject gas at S106.

The controller 130 may store as the initial value the output value of the odor sensor 112 that senses the pure air, and then may open the first valve 101-1 while closing the second valve 102-1 and the third valve 103-1, so that the pure air is supplied at predetermined time intervals to the odor sensor chamber 110. Thus, the odor sensor 112 may sense the pure air at the predetermined time intervals at S107.

Subsequently, the controller 130 compares with the initial value subsequent output values of the odor sensor 112 that senses the pure air at the predetermined time intervals (S108). When a difference in absolute value between the subsequent output value of the odor sensor 112 and the initial value is at a predetermined level or higher, the controller 130 determines the replacement of the odor sensor 112 due to the decrease in the performance of the odor sensor 112 and performs the alarming control for the replacement of the odor sensor 112 (S109).

Accordingly, the controller 130 may instruct the visual or audio alarming device 132 to issue the alarming signal to perform the alarming control for the replacement of the odor sensor 112. Thus, the user can recognize the need to replace the odor sensor 112 due to the decrease in the performance of the odor sensor 112.

In the method of measuring an odor according to the first embodiment of the present disclosure, the baseline that is utilized as the reference value for the output value of the odor sensor 112 can be accurately preset, and the delta value that represents the difference between the preset baseline and the output value of the odor sensor 112 that senses the odor-measurement-subject gas can be determined as the changed amount of the odor-measurement-subject gas. Thus, the accuracy of the odor measurement can be improved.

Second Embodiment

FIGS. 8 to 12 are views each illustrating an apparatus for measuring an odor according to a second embodiment of the present disclosure. Reference numerals 100 and 110-1 in each of the drawings depict the pre-chamber and a first odor sensor chamber, respectively.

The second embodiment of the present disclosure features a second odor sensor chamber 110-2 and a second odor sensor 112-2 for sensing fresh air that are separately arranged in a wired and wireless communication-enabled manner at a specific outside location (for example, an air intake part through which outside air flows into the vehicle, a cowl panel communicating with the outside air, a sunroof, or the like).

The pure air supply line 101 and the gas inflow line 102 for the inflow of the odor-measurement-subject gas are in parallel connected to one side of the pre-chamber 100.

In this case, the pure air supply tank 105 for supplying pure air (pure carbon dioxide or pure nitrogen) is connected to the pure air supply line 101, and the gas inflow line 102 is arranged in an open state inside a space (for example, an in-vehicle space) where the odor-measurement-subject gas is present.

In addition, the first valve 101-1 for supplying or blocking the flow of the pure air is mounted in an opening- and closing-enabled manner on the inlet port in the pure air supply line 101. Likewise, the second valve 102-1 for supplying or blocking the flow of the odor-measurement-subject gas is mounted in an opening- and closing-enabled manner on the inlet port in the gas inflow line 102.

The outlet port in the pure air supply line 101 and the outlet port in the gas inflow line 102 each are coupled to the first odor sensor chamber 110-1 through one gas flow line 104 in such a manner as to be enabled to be open into the first odor sensor chamber 110-1.

To this end, one gas flow line 104 is arranged along the lengthwise direction of the pre-chamber 100 inside the pre-chamber 100. The outlet port in the pure air supply line 101 and the outlet port in the gas inflow line 102 are coupled to one end of the gas flow line 104 in such a manner as to be enabled to be open into the gas flow line 104. The other end of the gas flow line 104 is coupled to the other side of the pre-chamber 100.

In addition, the gas flow line 104 and the first odor sensor chamber 110-1 are coupled to each other through the coupling pipe 120 in such a manner as to be enabled to be open into each other.

A first odor sensor 112-1 for sensing the pure air, the odor-measurement-subject gas, and the like is attached on an inner bottom surface of the first odor sensor chamber 110-1. The first odor sensor 112-1 may be one of an electro-chemical odor sensor, an electro-chemical odor sensor array, a bio-peptide type sensor, a sensor using amino acids, and other types of odor sensors.

In this case, the first odor sensor 112-1 is coupled to the controller 130 in a manner that can transmit the sensing signal. Thus, the first odor sensor 112-1 may transmit the signals, that is, the output values of the odor sensor 112 that senses the pure air, the odor-measurement-subject gas, the fresh air, and the like, to the controller 130.

Particularly, the second odor sensor chamber 110-2 employs a structure in which a fresh-air inlet port and a fresh-air outlet port are formed in one side and the other side, respectively, of the second odor sensor chamber 110-2. The second odor sensor chamber 110-2 is separately mounted at an outside position where the fresh is air seamlessly introduced. The second odor sensor 112-2 for sensing the fresh air is attached on an inner bottom surface of the second odor sensor chamber 110-2.

Accordingly, the second odor sensor 112-2 is connected to the controller 130 in a manner that can transmit the sensing signal. Thus, the second odor sensor 112-2 may transmit the signal, that is, the output value of the second odor sensor 112-2 that senses the fresh air, to the controller 130.

Therefore, the controller 130 may be configured to set a baseline that represents a reference value, as an output value of the first odor sensor 112-1 that senses the odor-measurement-subject gas, based on a signal that results from the first odor sensor 112-1 sensing the pure air that is supplied to the first odor sensor chamber 110-1, or a signal that results from the second odor sensor 112-2 sensing the fresh air that is supplied to the second odor sensor chamber 110-2.

Figure 10:
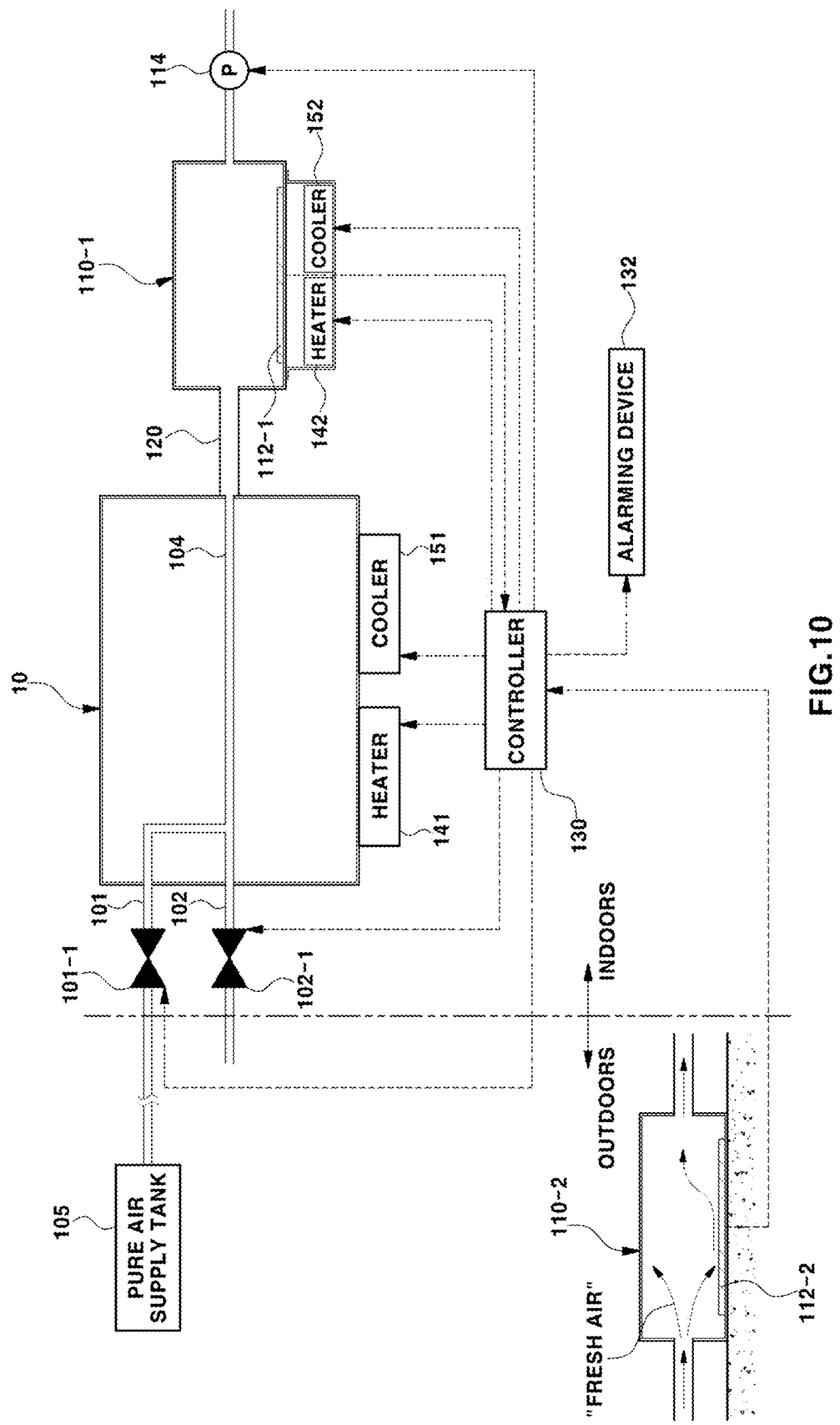

To this end, as illustrated in FIG. 10, the controller 130 is configured to set a baseline that is utilized as the reference value, as an output value of the second odor sensor 112-2 that senses the fresh air supplied to the second odor sensor chamber 110-2, when the fresh air that is the outside air is supplied to the second odor sensor chamber 110-2 in a state where the first valve 101-1 and the second valve 102-1 are closed.

As described above, the second odor sensor chamber 110-2 and the second odor sensor 112-2 for setting the baseline by sensing the fresh air are separately arranged at an external location where the fresh air seamlessly flows from the outside. This arrangement can allow for easier sensing of the fresh air and can reduce a sensing load on the first odor sensor 112-1, thereby ensuring the durability performance.

The odor measurement may be necessary at the location where the fresh air that is the outside air is contaminated. For example, the vehicle may pass by a livestock barn or passes through an industrial complex in which an odor occurs. In addition, the odor measurement may be necessary at the location where the fresh air that is the outside air is contaminated or absent, such as the inside of a manhole in which toxic gas is present, the inside of an airtight coal mine, the inside of an airtight submergence vehicle, the inside of an airtight submarine, the inside of an airtight spacecraft, the inside of an airtight space suit, or the like. In these cases, when the baseline that is utilized as the reference value is set as the output value of the second odor sensor 112-2 that senses the fresh air, the baseline that is utilized as the reference value may not be accurate. Consequently, a delta value (a changed amount of the odor-measurement-subject gas) that represents a difference between the baseline and the output value of the second odor sensor 112-2 may be inevitably inaccurate as before.

To solve this problem, in the case where the odor measurement is necessary at the location where the fresh air is contaminated or absent, the user can instruct the controller 130 to set the baseline based on the pure air, using an input means (for example, a switch or a menu button that is installed in the vehicle, or a corresponding application installed on a smart device).

Figure 12:
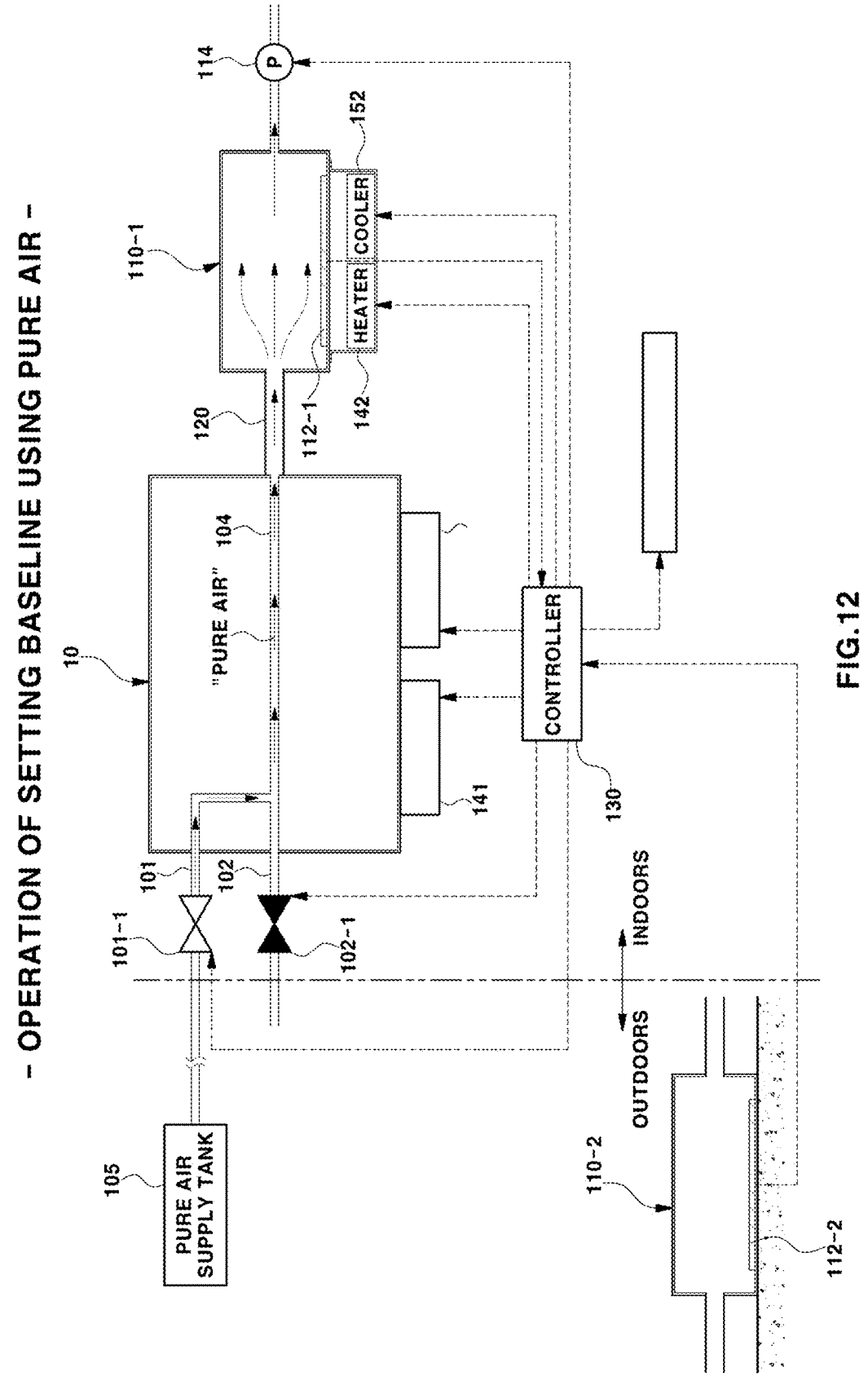

Accordingly, as illustrated in FIG. 12, the controller 130 is configured to open the first valve 101-1 while closing the second valve 102-1, in the case where the odor measurement is necessary at the location where the fresh air is contaminated or absent, so that the pure air is supplied from the pure air supply line 101 to the first odor sensor chamber 110-1 through the gas flow line 104 and the coupling pipe 120. Furthermore, the controller 130 is configured to set the baseline that is utilized as the reference value, as the output value of the first odor sensor 112-1 that senses the pure air supplied to the first odor sensor chamber 110-1.

As described above, after the baseline is set, the process of measuring an odor that is present in a specific internal space (for example, a space inside the vehicle, or the like) may be performed.

Figure 11:
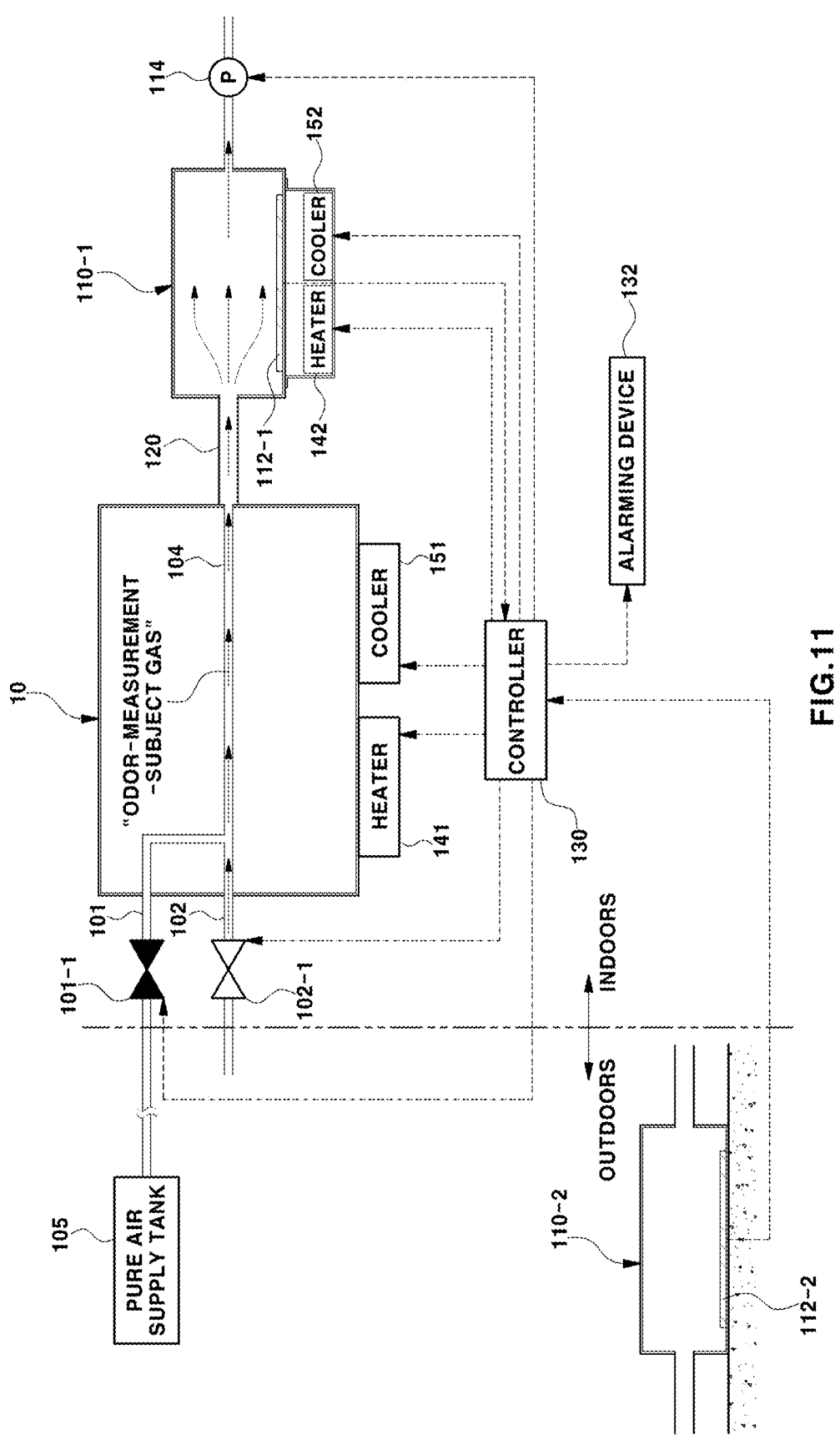

To this end, as illustrated in FIG. 11, the controller 130 may open the second valve 102-1 while closing the first valve 101-1, so that the odor-measurement-subject gas is supplied from the gas inflow line 102 to the first odor sensor chamber 110-1 through the gas flow line 104 and the coupling pipe 120. Furthermore, the controller 130 may be configured to compute a delta value that represents a difference between an output value of the first odor sensor 112-1 that senses the odor-measurement-subject gas supplied to the first odor sensor chamber 110-1 and the baseline that represents the reference value and to determine the computed delta value as the changed amount of the odor-measurement-subject gas.

In a case where the first odor sensor 112-1 is initially attached inside the first odor sensor chamber 110-1, in order to manage the lifetime and durability of the first odor sensor 112-1, it is preferred that an initial output value of the first odor sensor 112-1 is stored in the controller 130.

Figure 9:
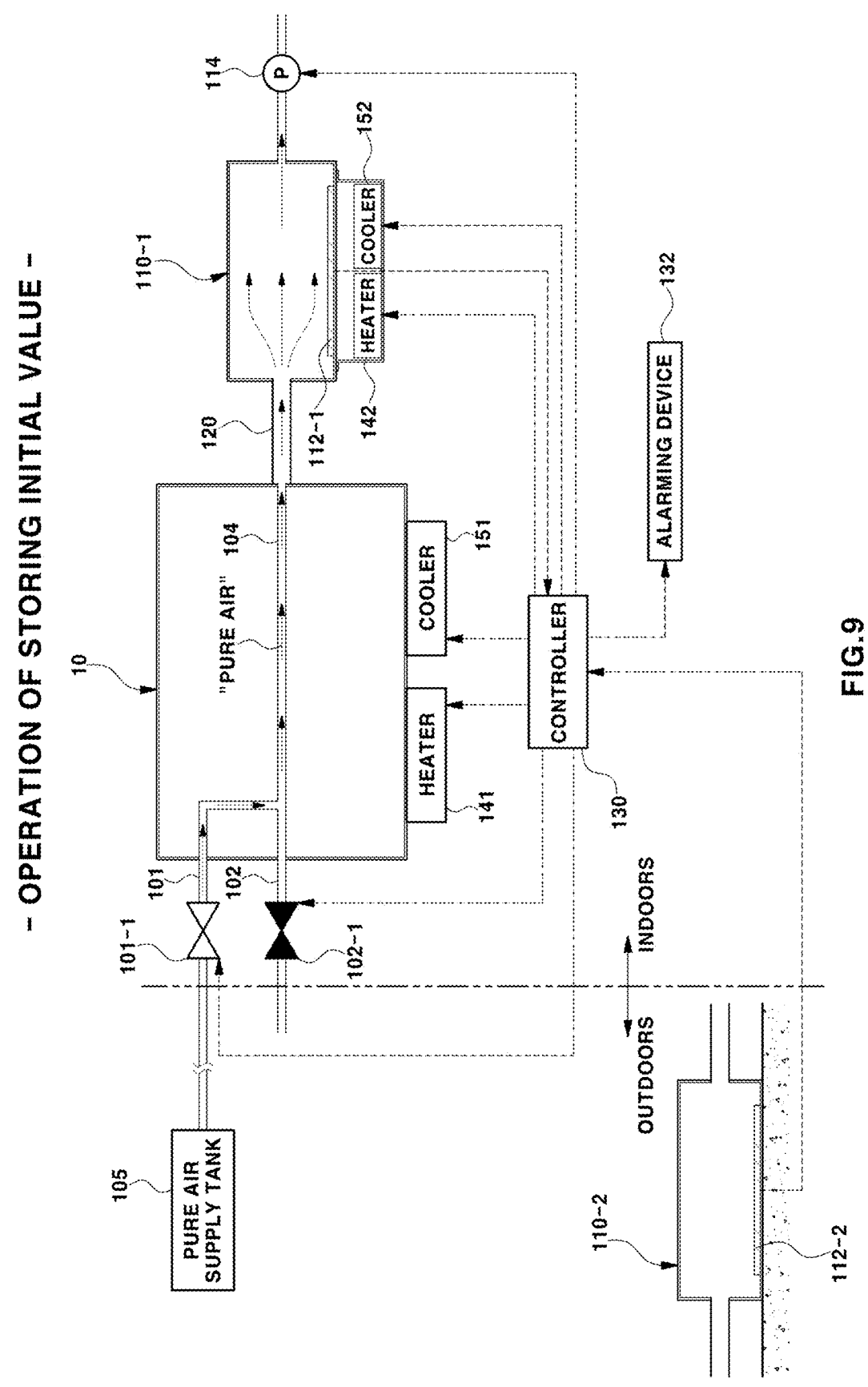
FIGS. 9, 10, 11, and 12 are schematic views each illustrating a state where the apparatus for measuring an odor according to the second embodiment of the present disclosure operates for the odor measurement.

To this end, as illustrated in FIG. 9, the controller 130 is configured to open the first valve 101-1 while closing the second valve 102-1 in the case where the first odor sensor 112-1 is initially attached inside the first odor sensor chamber 110-1, so that the pure air is supplied from the pure air supply line 101 to the first odor sensor chamber 110-1 through the gas flow line 104 and the coupling pipe 120. Furthermore, the controller 130 is configured to store the output value of the first odor sensor 112-1 that senses the pure air supplied to the first odor sensor chamber 110-1, as the initial value.

In this case, the more accumulated the usages of the first odor sensor 112-1, the more cracks occur on a surface of the first odor sensor 112-1, or the more foreign materials (dusts, gas particles, and the like) that cause a decrease in sensing performance build up on the surface of the first odor sensor 112-1. For these reasons, the first odor sensor 112-1 decreases in performance. Therefore, it is necessary to accurately determine a period with which the first odor sensor 112-1 is replaced.

To this end, the controller 130 may store as the initial value the output value of the first odor sensor 112-1 that senses the pure air, and may open the first valve 101-1 while closing the second valve 102-1, so that the pure air is supplied at predetermined time intervals to the first odor sensor chamber 110-1. Thus, the first odor sensor 112-1 may sense the pure air at the predetermined time intervals.

Therefore, the controller 130 is configured to store as the initial value the output value of the first odor sensor 112-1 that senses the pure air and then to compare, with the initial value subsequent output values of the first odor sensor 112-1 that senses the pure air at predetermined time intervals. Furthermore, the controller 130 is configured to determine replacement of the first odor sensor 112-1 due to a decrease in performance of the first odor sensor 112-1 and to perform alarming control for the replacement of the first odor sensor 112-1 when a difference between the subsequent output value of the first odor sensor 112-1 and the initial value is at a predetermined level or higher.

In this case, the controller 130 may instruct the visual or audio alarming device 132 to issue an alarming signal to perform the alarming control for the replacement of the first odor sensor 112-1.

It is preferred that the intake pump 114 for introducing the pure air and the odor-measurement-subject gas into the first odor sensor chamber 110-1 is coupled to an outlet port formed in the other side of the first odor sensor chamber 110-1.

Accordingly, by driving the intake pump 114, the pure air and the odor-measurement-subject gas can be easily introduced into the first odor sensor chamber 110-1 and, after the first odor sensor 112-1 performs sensing, can be discharged to the outside through the outlet port in the first odor sensor chamber 110-1.

When the first odor sensor 112-1 senses the pure air, the odor-measurement-subject gas, and the like, odor data that result from the measuring by the first odor sensor 112-1 may vary with the temperature or humidity of air or gas. Consequently, the accuracy of the measurement by the first odor sensor 112-1 may decrease. For this reason, it is preferred that the temperature or humidity of the air or gas (the pure air, the odor-measurement-subject gas, or the like) that is sensed by the first odor sensor 112-1 is consistently adjusted.

To this end, in order to heat the gas or the air that flows through the gas flow line 104, a first heater 141 and a first cooler 151 are mounted on the pre-chamber 100. The first heater 141 is turned on and off by the controller 130. The first cooler 151 is turned on and off by the controller 130 in order to cool the gas or air that flows through the gas flow line 104.

Accordingly, when the temperature of the air or gas (the pure air, the odor-measurement-subject gas, or the like) that flows through the gas flow line 104 is below the reference value, or when the humidity thereof is at or above the reference value, the controller 130 turns on the first heater 141 in order for the first heater 141 to perform the heating operation, based on the detection signal of the temperature and humidity sensor (not illustrated). In contrast, when the temperature of the air or gas (the pure air, the odor-measurement-subject gas, or the like) that flows through the gas flow line 104 is at or above the reference value, or when the humidity thereof is below the reference value, the controller 130 turns on the first cooler 151 in order for the first cooler 151 to perform the cooling operation, based on the detection signal of the temperature and humidity sensor. Thus, the temperature and the humidity of the gas or the air that flows through the gas flow line 104 can be consistently adjusted.

It Is preferred that the pre-chamber 100 is manufactured in such a manner to have a volume that facilitates transfer of warm air generated during heating or cold air generated during cooling to the gas or the air that flows through the gas flow line 104.

In this case, the temperature and the humidity of the air or gas (the pure air, the odor-measurement-subject gas, or the like) that flows through the gas flow line 104 are primarily adjusted by the first heater 141 or the first cooler 151, but may not be completely adjusted to a predetermined level.

Accordingly, the second heater 142 and the second cooler 152 may be further mounted at predetermined positions, respectively, on the first odor sensor chamber 110-1. The second heater 142 is turned on and off by the controller 130 in order to heat the inside of the odor sensor chamber 110-1. The second cooler 152 is turned on and off by the controller 130 in order to cool the inside of the odor sensor chamber 110-1.

With this configuration, the temperature and the humidity of the air or gas (the pure air, the odor-measurement-subject gas, or the like) that flows through the gas flow line 104 are primarily adjusted by the first heater 141 or the first cooler 151, and then the air or gas is supplied into the first odor sensor chamber 110-1. Thereafter, the temperature and the humidity of the air or gas that is introduced into the first odor sensor chamber 110-1 are secondarily adjusted by the heating operation of the second heater 142 and the cooling operation of the second cooler 152. Thus, the temperature and the humidity of the air or gas (the pure air, the odor-measurement-subject gas, the fresh air, or the like) that is sensed by the first odor sensor 112-1 can be completely adjusted to a predetermined level. Accordingly, the accuracy of the odor data that result from the measuring by the first odor sensor 112-1 can be ensured.

Sequential steps of the odor measurement by the apparatus for measuring an odor according to the second embodiment of the present disclosure are performed as follows.

Figure 13:
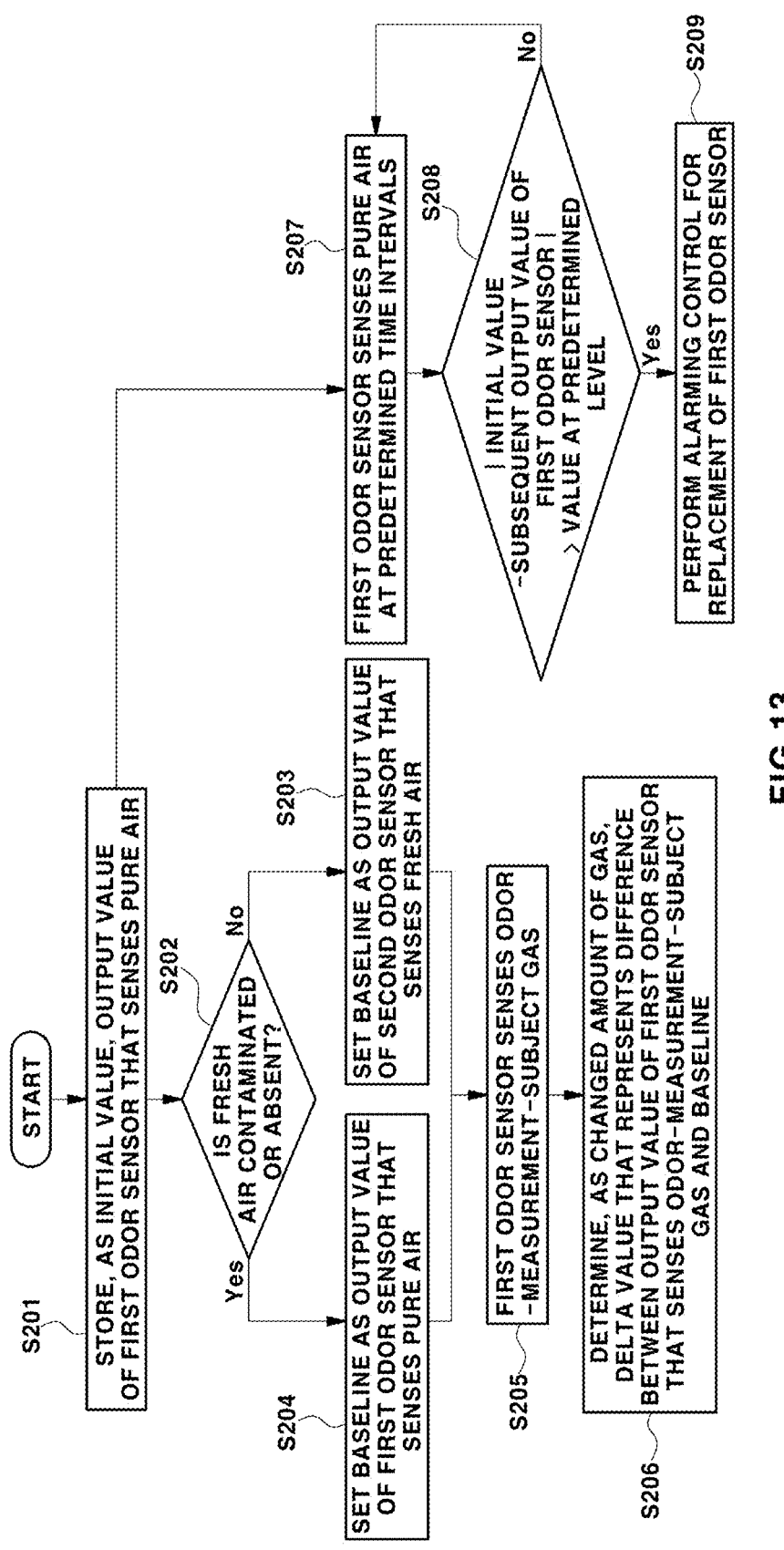
FIG. 13 is a flowchart illustrating a method of measuring an odor according to the second embodiment of the present disclosure.

FIG. 13 is a flowchart illustrating a method of measuring an odor according to the second embodiment of the present disclosure.

First, in the case where the first odor sensor 112-1 is initially attached inside the first odor sensor chamber 110-1, the first odor sensor 112-1 is set to sense the pure air, and the controller 130 stores as the initial value the output value of the first odor sensor 112-1 that senses the pure air at S201.

To this end, as illustrated in FIG. 9, in the case where the first odor sensor 112-1 is initially attached inside the first odor sensor chamber 110-1, the controller 130 opens the first valve 101-1 while closing the second valve 102-1, so that the pure air is supplied from the pure air supply line 101 to the first odor sensor chamber 110-1 through the gas flow line 104 and the coupling pipe 120. Furthermore, the controller 130 stores as the initial value the output value of the first odor sensor 112-1 that senses the pure air supplied to the first odor sensor chamber 110-1.

Subsequently, the user checks whether or not the fresh air that is the outside air is contaminated or whether or not fresh air is absent at S202.

In a case where the result of the checking is that the fresh air that is the outside air is clean without being contaminated, the baseline is set as the output value of the second odor sensor 112-2 that senses the fresh air at S203.

To this end, as illustrated in FIG. 10, in a state where the first valve 101-1 and the second valve 102-1 are closed, the controller 130 may set the baseline that is utilized as the reference value, as the output value of the second odor sensor 112-2 that senses the fresh air supplied to the second odor sensor chamber 110-2 and may store the output value of the second odor sensor 112-2.

In contrast, in the case where the fresh air that is the outside air is contaminated or absent, the baseline is set as the output value of the first odor sensor 112-1 that senses the pure air at S204.

To this end, as illustrated in FIG. 12, the controller 130 may open the first valve 101-1 while closing the second valve 102-1, so that the pure air is supplied from the pure air supply line 101 to the first odor sensor chamber 110-1 through the gas flow line 104 and the coupling pipe 120. Furthermore, the controller 130 may set the output value of the first odor sensor 112-1 that senses the pure air supplied to the first odor sensor chamber 110-1, as the base line that is utilized as the reference value, and may store the output value of the first odor sensor 112-1.

Next, the first odor sensor 112-1 senses odor-measurement-subject gases (for example, various nasty odors present inside the vehicle, nasty odors present in various industrial sites, and the like) at S205.

To this end, as illustrated in FIG. 11, the controller 130 opens the second valve 102-1 while closing the first valve 101-1, so that the odor-measurement-subject gas is supplied from the gas inflow line 102 to the first odor sensor chamber 110-1 through the gas flow line 104 and the coupling pipe 120. The first odor sensor 112-1 senses the odor-measurement-subject gas that is supplied to the first odor sensor chamber 110-1 and transmits the output value that results from the sensing, to the controller 130.

Subsequently, the controller 130 computes the delta value that represents the difference between the output value of the first odor sensor 112-1 that senses the odor-measurement-subject gas and the baseline that represents the reference value, and determines the computed delta value as the changed amount of the odor-measurement-subject gas at S206.

The controller 130 may store as the initial value the output value of the first odor sensor 112-1 that senses the pure air, and then may open the first valve 101-1 while closing the second valve 102-1, so that the pure air is supplied at predetermined time intervals to the first odor sensor chamber 110-1. Thus, the first odor sensor 112-1 may sense the pure air at the predetermined time intervals at S207.

Subsequently, the controller 130 compares with the initial value subsequent output values of the first odor sensor 112-1 that senses the pure air at the predetermined time intervals (S208). When a difference in absolute value between the subsequent output value of the first odor sensor 112-1 and the initial value is at a predetermined level or higher, the controller 130 determines the replacement of the first odor sensor 112-1 due to the decrease in the performance of the first odor sensor 112-1 and performs the alarming control for the replacement of the first odor sensor 112-1 at S209.

Accordingly, the controller 130 may instruct the visual or audio alarming device 132 to issue the alarming signal to perform the alarming control for the replacement of the first odor sensor 112-1. Thus, the user can recognize the need to replace the first odor sensor 112-1 due to the decrease in the performance of the first odor sensor 112-1.

In the method of measuring an odor according to the second embodiment of the present disclosure, the baseline that is utilized as the reference value for the output value of the first odor sensor 112-1 can be accurately preset, and the delta value that represents the difference between the preset baseline and the output value of the first odor sensor 112-1 that senses the odor-measurement-subject gas can be determined as the changed amount of the odor-measurement-subject gas. Thus, the accuracy of the odor measurement can be improved.

The apparatus for measuring an odor according to the present disclosure is capable of being mounted in a future mobility, such as a purpose-built vehicle (PBV) or an urban air mobility (UAM), as well as in a standard ground vehicle and of measuring various odors occurring in the standard ground vehicle and the future mobility. Thus, the apparatus can accurately analyze the actual causes of the occurrence of nasty odors, based on the odor data resulting from the measurement, thereby contributing to improving the odor-related emotional qualities of the vehicles and future mobility.

The apparatus for measuring an odor according to the present disclosure is capable of being mounted on a robot that is easily accessible to various industrial sites (for example, industrial sites in which a gas or nasty odor leakage occurs). Thus, the utility of the robot can be greatly enhanced, for example, by accurately measuring components and concentrations of odors that occur in these industrial sites.

The embodiments of the present disclosure are described above, but the scope of the claims of the present disclosure is not limited thereto. Various modifications and improvements that a person of ordinary skill in the art makes using the fundamental concept of the present disclosure that is defined in the following claims are also included in the scope of the claims of the present disclosure.

The invention claimed is:

1. An apparatus for measuring an odor, the apparatus comprising:
   a pre-chamber:
   a pure gas supply line coupled to one side of the pre-chamber;
   a gas inflow line configured to introduce odor-measurement-subject gas, the gas inflow line being coupled to the one side of the pre-chamber;
   a fresh air supply line coupled to the one side of the pre-chamber;
   a first valve mounted on the pure gas supply line;
   a second valve mounted on the gas inflow line;
   a third valve mounted on the fresh air supply line;
   an odor sensor chamber, the pure gas supply line, the gas inflow line, and the fresh air supply line being coupled to the odor sensor chamber so as to be enabled to be open into the odor sensor chamber;
   an odor sensor mounted inside the odor sensor chamber; and
   a controller configured to set a baseline that represents a reference value for an output value of the odor sensor that senses the odor-measurement-subject gas, based on a signal that results from the odor sensor sensing pure gas or fresh air that is supplied to the odor sensor chamber.

2. The apparatus of claim 1, further comprising:
   a gas flow line, one end of the gas line being coupled to the pure gas supply line, the gas inflow line, and the fresh air supply line so as to be enabled to be open into the pure gas supply line, the gas inflow line, and the fresh air supply line, and an other end of the gas flow line being coupled to an other side of the pre-chamber;

a coupling pipe coupled between the gas flow line and the odor sensor chamber so as to be enabled to be open into each other; and a pure gas supply tank coupled to the pure gas supply line.

3. The apparatus of claim 2, wherein a first heater that is configured to be turned on and off by the controller to heat gas or air that flows through the gas flow line, and a first cooler that is configured to be turned on and off by the controller to cool the gas or the air that flows through the gas flow line, are mounted on the pre-chamber.

4. The apparatus of claim 3, wherein a second heater that is configured to be turned on and off by the controller to heat the inside of the odor sensor chamber, and a second cooler that is configured to be turned on and off by the controller to cool the inside of the odor sensor chamber, are mounted on the odor sensor chamber.

5. The apparatus of claim 1, wherein the controller is configured to open the first valve while closing the second valve and the third valve, so that the pure gas is supplied from the pure gas supply line to the odor sensor chamber and to store as an initial value an output value of the odor sensor that senses the pure gas supplied to the odor sensor chamber.

6. The apparatus of claim 5, wherein the controller is configured to store as the initial value the output value of the odor sensor that senses the pure gas, then to compare with the initial value subsequent output values of the odor sensor that senses the pure air at predetermined time intervals and to perform alarming control for replacement of the odor sensor when a difference between the subsequent output value of the odor sensor and the initial value is at a predetermined level or higher.

7. The apparatus of claim 1, wherein the controller is configured to open the third valve while closing the first valve and the second valve, so that the fresh air that is outside air is supplied from the fresh air supply line to the odor sensor chamber and to set a baseline that is utilized as the reference value, as an output value of the odor sensor that senses the fresh air supplied to the odor sensor chamber.

8. The apparatus of claim 1, wherein the controller is configured to open the second valve while closing the first valve and the third valve, so that the odor-measurement-subject gas is supplied from the gas supply line to the odor sensor chamber, to compute a delta value that represents a difference between an output value of the odor sensor that senses the odor-measurement-subject gas supplied to the odor sensor chamber and a baseline that represents the reference value, and to determine the computed delta value as a changed amount of the odor-measurement-subject gas.

9. The apparatus of claim 1, wherein the controller is configured to open the first valve while closing the second valve and the third valve when odor measurement is necessary at a location where the fresh air that is outside air is contaminated, so that the pure gas is supplied from the pure gas supply line to the odor sensor chamber and to set a baseline that is utilized as the reference value, as an output value of the odor sensor that senses the pure gas supplied to the odor sensor chamber.

10. The apparatus of claim 1, wherein an intake pump for introducing the pure air, the odor-measurement-subject gas, and the fresh air into the odor sensor chamber is coupled to an outlet port formed in the other side of the odor sensor chamber.

11. An apparatus for measuring an odor, the apparatus comprising:

a pre-chamber;

a pure gas supply line coupled to one side of the pre-chamber;

a gas inflow line configured to introduce odor-measurement-subject gas, the gas inflow line being coupled to the one side of the pre-chamber;

a first valve mounted on the pure gas supply line;

a second valve mounted on the gas inflow line;

a first odor sensor chamber, the pure gas supply line and the gas inflow line being coupled to the first odor sensor chamber so as to be enabled to be open into the first odor sensor chamber;

a first odor sensor mounted inside the first odor sensor chamber;

a second odor sensor chamber having a structure in which a fresh-air inlet port is positioned in one side of the second odor sensor chamber, and a fresh-air outlet port positioned in an other side of the second odor sensor chamber, the second odor sensor chamber being separately mounted at an outside position where fresh air is seamlessly introduced;

a second odor sensor mounted inside the second odor sensor chamber; and a controller configured to set a baseline that represents a reference value for an output value of the first odor sensor that senses the odor-measurement-subject gas, based on a signal that results from the first odor sensor sensing pure air that is supplied to the first odor sensor chamber or a signal that results from the second odor sensor sensing the fresh air that is supplied to the second odor sensor chamber.

12. The apparatus of claim 11, further comprising:

a gas flow line, one end of the gas flow line being coupled to the pure gas supply line and the gas inflow line so as to be enabled to be open into the pure gas supply line and the gas inflow line, and an other end of the gas flow line being coupled to an other side of the pre-chamber;

a coupling pipe coupled between the gas flow line and the first odor sensor chamber so as to be enabled to be open into each other; and a pure gas supply tank coupled to the pure gas supply line.

13. The apparatus of claim 12, wherein a first heater that is configured to be turned-on and off by the controller to heat gas or air that flows through the gas flow line, and a first cooler that is configured to be turned on and off by the controller to cool the gas or the air that flows through the gas flow line, are mounted on the pre-chamber.

14. The apparatus of claim 13, wherein a second heater that is configured to be turned on and off by the controller in order to heat the inside of the first odor sensor chamber, and a second cooler that is configured to be turned on and off by the controller in order to cool the inside of the first odor sensor chamber, are mounted on the first odor sensor chamber.

15. The apparatus of claim 11, wherein the controller is configured to open the first valve while closing the second valve, so that the pure gas is supplied from the pure gas supply line to the first odor sensor chamber and to store as an initial value an output value of the first odor sensor that senses the pure gas supplied to the first odor sensor chamber.

16. The apparatus of claim 15, wherein the controller is configured to store as the initial value the output value of the first odor sensor that senses the pure gas, then to compare with the initial value subsequent output values of the first odor sensor that sense the pure air at predetermined time intervals and to perform alarming control for replacement of the first odor sensor when a difference between the subsequent output value of the first odor sensor and the initial value is at a predetermined level or higher.

17. The apparatus of claim 11, wherein the controller is configured to set a baseline that is utilized as the reference value, as an output value of the second odor sensor that senses the fresh air supplied to the second odor sensor chamber.

18. The apparatus of claim 11, wherein the controller is configured to open the second valve while closing the first valve, so that the odor-measurement-subject gas is supplied from the gas supply line to the first odor sensor chamber, to compute a delta value that represents a difference between an output value of the first odor sensor that senses the odor-measurement-subject gas supplied to the first odor sensor chamber and a baseline that represents the reference value, and to determine the computed delta value as a changed amount of the odor-measurement-subject gas.

19. The apparatus of claim 11, wherein the controller is configured to open the first valve while closing the second valve when odor measurement is performed at a location where the fresh air that is outside air is contaminated, so that the pure gas is supplied from the pure gas supply line to the first odor sensor chamber and to set a baseline that is utilized as the reference value, as an output value of the first odor sensor that senses the pure gas supplied to the first odor sensor chamber.

20. The apparatus of claim 11, wherein an intake pump for introducing the pure gas and the odor-measurement-subject gas into the first odor sensor chamber is coupled to an outlet port formed in the other side of the first odor sensor chamber.

\* \* \* \* \*